(12) United States Patent
Miller et al.

(10) Patent No.: US 7,700,111 B2
(45) Date of Patent: Apr. 20, 2010

(54) AUDITORY NERVE PROTECTION AND RE-GROWTH

(75) Inventors: Josef M. Miller, Ann Arbor, MI (US); Richard A. Altschuler, Ann Arbor, MI (US); Yehoash Raphael, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 67 days.

(21) Appl. No.: 10/345,731

(22) Filed: Jan. 16, 2003

(65) Prior Publication Data

US 2004/0247570 A1 Dec. 9, 2004

Related U.S. Application Data

(60) Provisional application No. 60/349,799, filed on Jan. 17, 2002, provisional application No. 60/351,870, filed on Jan. 25, 2002.

(51) Int. Cl.
*A61F 13/00* (2006.01)
*A61K 39/00* (2006.01)
*A61N 1/00* (2006.01)

(52) U.S. Cl. .................. 424/198.1; 424/422; 607/57

(58) Field of Classification Search .................. None
See application file for complete search history.

(56) References Cited

OTHER PUBLICATIONS

Altschuler RA et al. Rescue and regrowth of sensory nerves following deafferentation by neurotrophic factors, 1999, Ann NY Acad Sci, 884:305-311.*
Ryan AF. Molecular studies of hair cell development and survival, 2002, Audiol Neurootol, 7:138-140.*
NIH Publication No. 00-4798, Cochlear Implants, NIDCD, Mar. 2000.*
Mitchell et al. Effects of chronic high-rate electrical stimulation on the cochlea and eighth nerve in the deafened guinea pig. Hearing Research, 1997, 105: 30-43.*
Leake PA et al. Chronic electrical stimulation by a cochlear implant promotes survival of spiral ganglion neurons after neonatal deafness. J. Comp Neurol. 1999; 412: 543-562.*
Marzella Pl & Clark GM. Growth factors, auditory neurones and cochlear implants: A review. Acta Otolaryngol (Stockh) 1999; 119: 407-412.*
Kopke et al., Annals of the New York Academy of Sciences, 884: 171-191, Nov. 28, 1999.*
Gallego et al., Electroencephalography and Clinical Neurophysiology 108:521 [1998.

Kiang et al., Acta Oto Laryngologica 87:204 [1979].
Baldi et al., European Journal of Neuroscience 12:2281 [2000].
White et al., Hear Res. 141:12 [2000].
Capurso et al., J Neurosci 17:7372 [1997].
Gong et al., Neuroscience Letters 263:153 [1999].
Hartshorn et al., Otolaryngol Head Neck Surg., 104:311 [1991].
Ming et al., Neuron, 29:441 [2001].
Hegarty et al., J. Neurosci., 17:1959 [1997].
Miller et al., Hear Res., 151:1 [2001].
Rathbone et al., Progress in Neurobiology 59:663 [1999].
Shepherd et al., Hear Res 66:108 [1993].
Miller et al., Current Opinion in Otolaryngology Head and Neck Surgery, 6:301 [1998].
Di Iorio et al., Experimental Neurology, 169:392 [2001].
Di Iorio et al. Drug Dev. Res., 52:303 [2001].
Prieskorn and Miller, Hearing Res., 140:212 [2000].
Stover et al., Hear Res., 136:124 [1999].
Brown et al., Hear Res., 70:167 [1993].
Cohen Salmon et al., PNASE 94:14450 [1997].
Miller et al., Scandinavian Audiology Supplementum 48:53 [1998].
Kopke et al., Annals of the New York Academy of Sciences 884:171 [1999].
Quirk et al., Hear Res., 52:217 [1991].
Yamasoba et al., Brain Res. 815:317 [1999].
Mitchell et al., Hear Res., 105:30 [1997].
Leake et al., Hear Res., 64:99 [1992].
Lim et al., Hear Res., 69:146 [1993].
Altschuler, Hear. Res., 31:173 [1991].
Ohinata et al., Brain Res. 878, [2000].
Neary et al., "Trophic actions of extracellular nucleotides and nucleosides on glial and neuronal cells," Trends Neurosci 19:13 [1996].
Kingma et al., "Chronic drug infusion into the scala tympani of the guinea pig cochlea," J. Neurosci. Methods 45:127 [1992].
Shoji et al., "Glial cell line-derived neurotrophic factor has a dose dependent influence on noise-induced hearing loss in the guinea pig cochlea," Hearing Res. 142:41; [2000].
Shoji et al., "Differential protective effects of neurotrophins in the attenuation of noise-induced hair cell loss," Hearing Res. 146:134 [2000].
Scheibe et al., European Archives of Oto Rhino Laryngology 250:281 [1993].

* cited by examiner

*Primary Examiner*—John D. Ulm
*Assistant Examiner*—Stacey MacFarlane
(74) *Attorney, Agent, or Firm*—Casimir Jones, S.C.

(57) ABSTRACT

The present invention relates to compositions and methods for the protection and restoration of hearing. In particular, the present invention relates to treatments to facilitate the protection and re-growth of the auditory nerve. The present invention further provides methods of preventing hair cell loss and the accompanying loss in hearing. The present invention thus provides novel interventions for a variety of hearing impairments.

6 Claims, 21 Drawing Sheets

Input-output curves of P1 amplitudes

Input-output curves of P1 amplitudes

Input-output curves of P1 amplitudes

PTS ONLY

AUDITORY NERVE PROTECTION AND RE-GROWTH

This application claims priority to U.S. provisional patent application Ser. No. 60/349,799, filed Jan. 17, 2002 and U.S. provisional patent application Ser. No. 60/351,870, filed Jan. 25, 2002.

This invention was made with government support under Grant No. DC03820 awarded by the National Institutes of Health. The Government has certain rights in the invention.

FIELD OF THE INVENTION

The present invention relates to compositions and methods for the protection and restoration of hearing. In particular, the present invention relates to treatments to facilitate the protection and re-growth of the auditory nerve.

BACKGROUND OF THE INVENTION

Hearing impairment is the United State's number one disability. It has been estimated to compromise the quality of life and communication in more than 30 million Americans, and approximately 1 billion individuals worldwide. With the increase in longevity in life and the association of hearing impairment with aging, this disability is increasing in incidence and prevalence. In children, it severely affects education and future employment opportunities. In a working individual, it compromises the quality of life, job satisfaction, and productivity; and in the elderly, it leads to isolation and increased medical costs.

Sensorineural hearing loss is better known as nerve deafness. This is behind 95% of all hearing problems. It usually happens because the tiny, sound-transmitting structures deep within the ear wear down or get damaged. Sound enters the inner ear, but it doesn't get sent to the brain in the right way. Nerve deafness can be caused by loud noise, use of ear-damaging or ototoxic drugs, infections like measles and meningitis, an accident or trauma, or a birth or hereditary defect. Treatments for nerve deafness (e.g., hearing aids), allow for improved hearing and improved quality of life in some individuals.

The remaining 5% of hearing problems are due to conductive hearing loss. In these conditions, sound is not transferred from the outer to the inner ear. Conductive hearing loss can result from a punctured eardrum, severely impacted earwax (cerumen), head trauma, birth defects, or heredity.

For patients with profound deafness, cochlear implants may provide some sound and often prove quite helpful. Though they can't restore natural hearing, cochlear implants produce hearing sensations in the ear. While cochlear implants have provided a huge advance in the treatment of profound hearing impairment, patient performance remains highly variable, and even in the best cases, implant performance is far below that of the native, normal inner ear. Thus, methods of treating deafness and improving the outcome of profoundly deaf patients are needed.

SUMMARY OF THE INVENTION

The present invention relates to compositions and methods for the protection and restoration of hearing. In particular, the present invention relates to treatments to facilitate the protection and re-growth of the auditory nerve. Accordingly, in some embodiments, the present invention provides a method of maintaining viability of spiral ganglion cells, comprising providing spiral ganglion cells, wherein the spiral ganglion cells are maintained under conditions such that the spiral ganglion cells do not maintain viability; at least one neurotrophin; and a device configured for the administration of continuous electrical stimulation; and administering the neurotrophin and the continuous electrical stimulation under conditions such that the viability of the spiral ganglion cells is maintained. In some embodiments, the density of the ganglion cells is at least 15% greater than the density in the absence of administering the neurotrophin and the continuous electrical stimulation for at least 44 days following administration. In some embodiments, the density of the ganglion cells is at least 20% greater than the density in the absence of administering the neurotrophin and the continuous electrical stimulation for at least 44 days following administration. In some embodiments, the density of the ganglion cells is at least 30% greater than the density in the absence of administering the neurotrophin and the continuous electrical stimulation for at least 44 days following administration. In some embodiments, the spiral ganglion cells are part of an ear of an animal. In some embodiments, the ear is lacking inner hair cells. In some embodiments, the neurotrophin is selected from the group including, but not limited to, glial cell line-derived neurotrophic factor, brain-derived neurotrophic factor, neurotrophin-3, neurotrophin-4/5, and ciliary neurotrophic factor. In some embodiments, the neurotrophin is administered locally to the ear of the animal. In some embodiments, the administered locally is via an osmotic pump implanted in the ear of the animal. In other embodiments, the administered locally is via a gene expressing a neurotrophin. In some embodiments, the device comprises an electrode inserted into a cochlear implant implanted in the ear of the animal.

The present invention further provides a method of promoting growth of spiral ganglion cells, comprising providing spiral ganglion cells; a device configured for the administration of continuous electrical stimulation; and administering the continuous electrical stimulation with the device under conditions such that the growth of the spiral ganglion cells is promoted. In some embodiments, the spiral ganglion cells are part of an ear of an animal. In some embodiments, the device comprises an electrode, and wherein the electrode is inserted into a cochlear implant implanted in the ear of the animal. In some embodiments, a neurotrophin is administered concurrently with the continuous electrical stimulation. In some embodiments, the neurotrophin is selected from the group including, but not limited to, glial cell line-derived neurotrophic factor, brain-derived neurotrophic factor, neurotrophin-3, neurotrophin-4/5, and ciliary neurotrophic factor. In some embodiments, the neurotrophin is administered locally to the ear. In some embodiments, the administered locally is via an osmotic pump implanted in the ear of the animal. In other embodiments, the administered locally is via a gene expressing a neurotrophin.

The present invention additionally provides a kit for use in promoting growth of spiral ganglion cells, comprising a device configured for the administration of continuous electrical stimulation to the inner ear; and instructions for using the kit for promoting growth of spiral ganglion cells. In some embodiments, the device comprises an electrode configured for insertion into a cochlear implant. In some embodiments, the kit further comprises a neurotrophin. In some embodiments, the neurotrophin is selected from the group including, but not limited to, glial cell line-derived neurotrophic factor, brain-derived neurotrophic factor, neurotrophin-3, neurotrophin-4/5, and ciliary neurotrophic factor.

The present further provides a kit for use in maintaining viability of spiral ganglion cells, comprising a device configured for the administration of chronic electrical stimulation to the inner ear; and at least one neurotrophin. In some embodiments, the kit further comprises instructions for using the kit for marinating viability of spiral ganglion cells. In some embodiments, the device comprises an electrode configured for insertion into a cochlear implant. In some embodiments, the neurotrophin is selected from the group including, but not limited to, glial cell line-derived neurotrophic factor, brain-derived neurotrophic factor, neurotrophin-3, neurotrophin-4/5, and ciliary neurotrophic factor.

GENERAL DESCRIPTION

Figure 1:
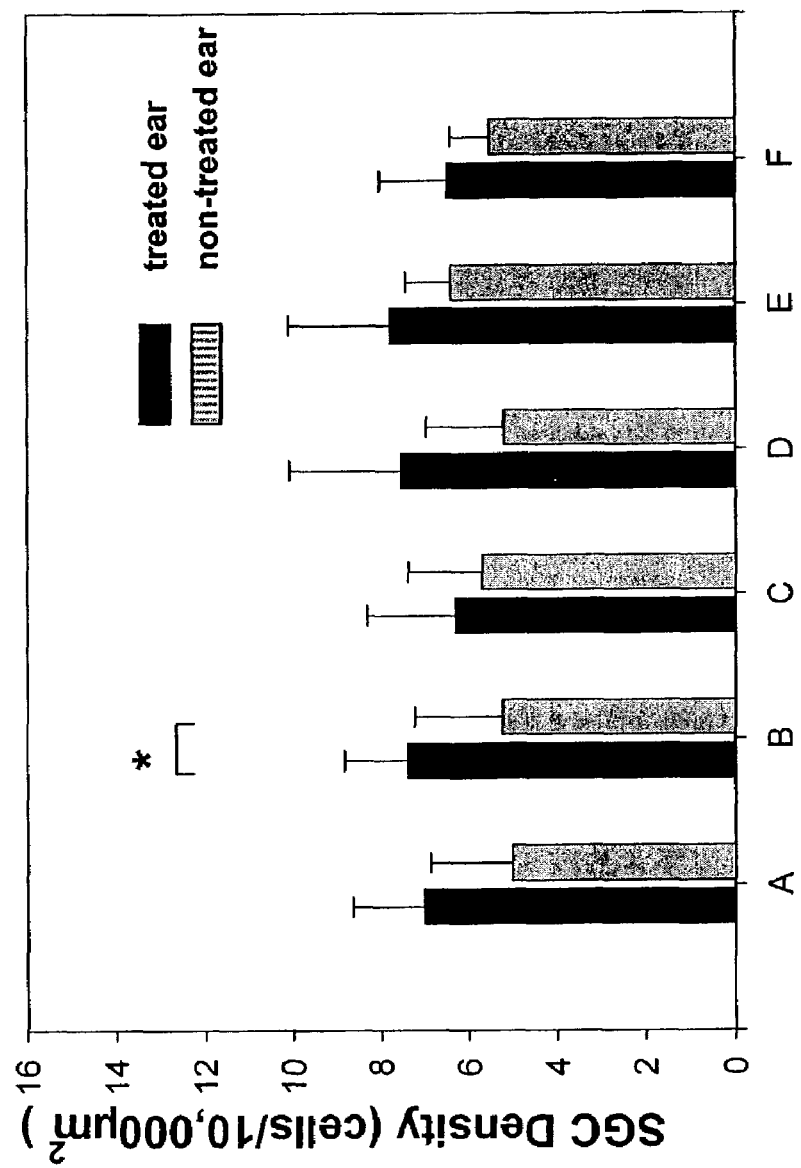
FIG. 1 shows a comparison between treated and non-treated ears in the ES group (mean±SD). The density of surviving SGCs in treated and non-treated ears is shown in each one of the areas (A-F) analyzed.

The ability to prevent and treat hearing impairment is benefited by an understanding of the processes underlying such impairment. To that end, animal models have been developed for two common causes of hearing loss: acoustic trauma (noise-induced hearing loss, NIHL) and pharmacological trauma (ototoxic hearing loss). Following both acoustic and ototoxic challenge, the earliest and most striking histological changes are observed within the organ of Corti, with loss of the hair cells, which serve as the sensory receptors of the auditory system (Lim, Annals of Otology, Rhinology and Laryngology 85:740 [1976]). Subsequently, degenerative changes are noted within the auditory nerve, including progressive loss of spiral ganglion cells (SGC) (Webster and Webster, Brain Research, 212:17 [1981]), as well as retrograde degeneration of the peripheral processes of surviving cells (Spoendlin, Annals of Otology, Rhinology, & Laryngology S112:76 [1984]).

Accordingly, the present invention provides treatments to effectively and safely promote the survival and regrowth of the auditory nerve. This treatment provides use in therapies for severely and profoundly hearing impaired patients, who are candidates for cochlear prosthesis (bionic ear) implantation. The cochlear implant, which is the therapy of choice for the deaf patient, consists of a series of electrodes that are surgically introduced into the inner ear to directly stimulate the auditory nerves to the brain, bypassing damaged inner ear receptors. The prosthesis includes a sound transducer and signal processor that converts sound cues to electrical pulses which activate the auditory nerve fibers, providing an encoded representation of the acoustic environment. The benefit of cochlear implants is highly dependent upon survival and excitability of the auditory nerve as well as a close relationship or contact between electrodes of the implant with fibers of the auditory nerve (See e.g., Gallego et al., Electroencephalography and Clinical Neurophysiology 108:521 [1998]; Kiang et al., Acta Oto-Laryngologica 87:204 [1979]). The post-deafening degenerative changes in the auditory nerve both decrease the number of target neurons available for the implant to stimulate, and, as the peripheral processes degenerate, remove the persisting neurons from the site of the electrode implant.

In the auditory system, these degenerative changes have immediate implications for the function of the cochlear implant. The treatments provided by the present invention have significant benefits for the profoundly deaf. This population is estimated at 2 million in the USA and 600 million worldwide. To date, approximately 45,000 patients have received cochlear implants, a population that is expected to grow rapidly given the demonstrated efficacy of the implants in restoring some degree of auditory perception.

It is contemplated that future treatments for the profoundly deaf will include tissue engineering within the inner ear resulting in regeneration of auditory hair cells. However, restoration of these sensory receptors will result in functional improvement only in those individuals for which the necessary wiring exists to relay information centrally. Accordingly, the methods of the present invention further provide for innervation following regeneration of the sensory hair cells.

The present invention is not limited to a particular mechanism. Indeed, an understanding of the mechanism is not necessary to practice the present invention. Nonetheless, it is contemplated that auditory nerve degeneration may be a primary process in some etiologies of hearing loss. Thus, the methods of the present invention further find use in restoring hearing in individuals for whom auditory nerve degeneration is the primary event.

The present invention is not limited to a particular mechanism. Indeed, an understanding of the mechanism is not necessary to practice the present invention. Nonetheless, it is contemplated that age-related hearing loss is believed to involve, at least in part, age-related degeneration of spiral ganglion cell peripheral processes (White et al., Hear Res. 141:12 [2000]). Accordingly, it is contemplated that the methods of the present invention find use in reducing or eliminating age-related changes in hearing acuity.

The degenerative process observed in the inner ear following deafferentation (loss of receptor input) is not unique to the auditory system. Dependence of neuron survival on intact afferent input is a common theme within the central nervous system (See e.g., Baldi et al., European Journal of Neuroscience 12:2281 [2000]; Capurso et al., J Neurosci 17:7372 [1997]). The present invention is not limited to a particular mechanism. Indeed, an understanding of the mechanism is not necessary to practice the present invention. Nonetheless, it is contemplated that treatment methods of the present invention are applicable to neurodegeneration occurring in other regions of the nervous system, both centrally and peripherally.

DEFINITIONS

To facilitate an understanding of the present invention, a number of terms and phrases are defined below:

As used herein, the term "neurotrophin" refers to any compound that has a stimulating or positive effect on neurons. For example, in some embodiments, neurotrophins stimulate the growth of neurons. In other embodiments, neurotrophins prevents the death of neurons (e.g., maintain the viability). In some embodiments, neurotrophins are used in conjunction with the administration of continuous electrical stimulation to maintain the viability or promote the growth of neurons (e.g., spiral ganglion cells).

As used herein, the terms "chronic electrical stimulation" and "continuous electrical stimulation" refer to the long-term continuous administration of electrical stimulation (e.g., to the ear) without lapses. "Continuous electrical stimulation" includes both constant electrical current and pulsating electrical current.

As used herein, the term "a device configured for the administration of continuous electrical stimulation" refers to a source of electrical stimulation (e.g., an electrode) configured for insertion into the inner ear of a subject. In some embodiments, the device is inserted into a cochlear implant.

As used herein, the term "administered locally" refers to a treatment (e.g., a drug) that is administered directly to the area to be treated (e.g., the inner ear or cochlea). Local administration is in contrast to "systemic administration" where a drug is administered systemically (e.g., via the bloodstream) to an entire organism. Local administration to the inner ear is performed by any suitable method including, but not limited to, gene therapy with a vector that is only expressed in the ear, via an implanted osmotic pump, via direct injection into the cochlea, or indirect administration via the middle ear.

As used herein, the term "under conditions such that said viability of said spiral ganglion cells is prevented" refers to treatment conditions of the present invention that result in an the death of fewer spiral ganglion cells over time relative to the absence of the treatment.

As used herein, the term "under conditions such that growth of said spiral ganglion cells is promoted" refers to treatment conditions of the present invention that result in an increased production of new spiral ganglion cells relative to the number generated in the absence of the treatment and/or an increase in length of the existing neurons.

As used herein, the term "instructions for using said kit for promoting growth of spiral ganglion cells" and "instructions for using said kit for preventing the death of spiral ganglion cells" includes instructions for using the devices and neurotrophins contained in the kit for the intended use. In some embodiments, the instructions further comprise the statement of intended use required by the U.S. Food and Drug Administration (FDA) in labeling pharmaceutical products.

The term "epitope" as used herein refers to that portion of an antigen that makes contact with a particular antibody.

When a protein or fragment of a protein is used to immunize a host animal, numerous regions of the protein may induce the production of antibodies which bind specifically to a given region or three-dimensional structure on the protein; these regions or structures are referred to as "antigenic determinants". An antigenic determinant may compete with the intact antigen (i.e., the "immunogen" used to elicit the immune response) for binding to an antibody.

The terms "specific binding" or "specifically binding" when used in reference to the interaction of an antibody and a protein or peptide means that the interaction is dependent upon the presence of a particular structure (i.e., the antigenic determinant or epitope) on the protein; in other words the antibody is recognizing and binding to a specific protein structure rather than to proteins in general. For example, if an antibody is specific for epitope "A," the presence of a protein containing epitope A (or free, unlabelled A) in a reaction containing labeled "A" and the antibody will reduce the amount of labeled A bound to the antibody.

As used herein, the terms "non-specific binding" and "background binding" when used in reference to the interaction of an antibody and a protein or peptide refer to an interaction that is not dependent on the presence of a particular structure (i.e., the antibody is binding to proteins in general rather that a particular structure such as an epitope).

As used herein, the term "subject" refers to any animal (e.g., a mammal), including, but not limited to, humans, non-human primates, rodents, and the like, which is to be the recipient of a particular treatment. Typically, the terms "subject" and "patient" are used interchangeably herein in reference to a human subject.

As used herein, the term "non-human animals" refers to all non-human animals including, but are not limited to, vertebrates such as rodents, non-human primates, ovines, bovines, ruminants, lagomorphs, porcines, caprines, equines, canines, felines, aves, etc.

As used herein, the term "gene transfer system" refers to any means of delivering a composition comprising a nucleic acid sequence to a cell or tissue. For example, gene transfer systems include, but are not limited to, vectors (e.g., retroviral, adenoviral, adeno-associated viral, and other nucleic acid-based delivery systems), microinjection of naked nucleic acid, polymer-based delivery systems (e.g., liposome-based and metallic particle-based systems), biolistic injection, and the like. As used herein, the term "viral gene transfer system" refers to gene transfer systems comprising viral elements (e.g., intact viruses, modified viruses and viral components such as nucleic acids or proteins) to facilitate delivery of the sample to a desired cell or tissue. As used herein, the term "adenovirus gene transfer system" refers to gene transfer systems comprising intact or altered viruses belonging to the family Adenoviridae.

As used herein, the term "site-specific recombination target sequences" refers to nucleic acid sequences that provide recognition sequences for recombination factors and the location where recombination takes place.

As used herein, the term "nucleic acid molecule" refers to any nucleic acid containing molecule, including but not limited to, DNA or RNA. The term encompasses sequences that include any of the known base analogs of DNA and RNA including, but not limited to, 4-acetylcytosine, 8-hydroxy-N-6-methyladenosine, aziridinylcytosine, pseudoisocytosine, 5-(carboxyhydroxylmethyl)uracil, 5-fluorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine.

The term "gene" refers to a nucleic acid (e.g., DNA) sequence that comprises coding sequences necessary for the production of a polypeptide, precursor, or RNA (e.g., rRNA, tRNA). The polypeptide can be encoded by a full length coding sequence or by any portion of the coding sequence so long as the desired activity or functional properties (e.g., enzymatic activity, ligand binding, signal transduction, immunogenicity, etc.) of the full-length or fragment are retained. The term also encompasses the coding region of a structural gene and the sequences located adjacent to the coding region on both the 5' and 3' ends for a distance of about 1 kb or more on either end such that the gene corresponds to the length of the full-length mRNA. Sequences located 5' of the coding region and present on the mRNA are referred to as 5' non-translated sequences. Sequences located 3' or downstream of the coding region and present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

As used herein, the term "heterologous gene" refers to a gene that is not in its natural environment. For example, a heterologous gene includes a gene from one species introduced into another species. A heterologous gene also includes a gene native to an organism that has been altered in some way (e.g., mutated, added in multiple copies, linked to non-native regulatory sequences, etc). Heterologous genes are distinguished from endogenous genes in that the heterologous gene sequences are typically joined to DNA sequences that are not found naturally associated with the gene sequences in the chromosome or are associated with portions of the chromosome not found in nature (e.g., genes expressed in loci where the gene is not normally expressed).

As used herein, the term "gene expression" refers to the process of converting genetic information encoded in a gene into RNA (e.g., mRNA, rRNA, tRNA, or snRNA) through "transcription" of the gene (i.e., via the enzymatic action of an RNA polymerase), and for protein encoding genes, into protein through "translation" of mRNA. Gene expression can be regulated at many stages in the process. "Up-regulation" or "activation" refers to regulation that increases the production of gene expression products (i.e., RNA or protein), while "down-regulation" or "repression" refers to regulation that decrease production. Molecules (e.g., transcription factors) that are involved in up-regulation or down-regulation are often called "activators" and "repressors," respectively.

In addition to containing introns, genomic forms of a gene may also include sequences located on both the 5' and 3' end of the sequences that are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers that control or influence the transcription of the gene. The 3' flanking region may contain sequences that direct the termination of transcription, post-transcriptional cleavage and polyadenylation.

The term "wild-type" refers to a gene or gene product isolated from a naturally occurring source. A wild-type gene is that which is most frequently observed in a population and is thus arbitrarily designed the "normal" or "wild-type" form of the gene. In contrast, the term "modified" or "mutant" refers to a gene or gene product that displays modifications in sequence and or functional properties (i.e., altered characteristics) when compared to the wild-type gene or gene product. It is noted that naturally occurring mutants can be isolated; these are identified by the fact that they have altered characteristics (including altered nucleic acid sequences) when compared to the wild-type gene or gene product.

As used herein, the terms "nucleic acid molecule encoding," "DNA sequence encoding," and "DNA encoding" refer to the order or sequence of deoxyribonucleotides along a strand of deoxyribonucleic acid. The order of these deoxyribonucleotides determines the order of amino acids along the polypeptide (protein) chain. The DNA sequence thus codes for the amino acid sequence.

As used herein, the terms "an oligonucleotide having a nucleotide sequence encoding a gene" and "polynucleotide having a nucleotide sequence encoding a gene," means a nucleic acid sequence comprising the coding region of a gene or in other words the nucleic acid sequence that encodes a gene product. The coding region may be present in a cDNA, genomic DNA or RNA form. When present in a DNA form, the oligonucleotide or polynucleotide may be single-stranded (i.e., the sense strand) or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present invention may contain endogenous enhancers/promoters, splice junctions, intervening sequences, polyadenylation signals, etc. or a combination of both endogenous and exogenous control elements.

A gene may produce multiple RNA species that are generated by differential splicing of the primary RNA transcript. cDNAs that are splice variants of the same gene will contain regions of sequence identity or complete homology (representing the presence of the same exon or portion of the same exon on both cDNAs) and regions of complete non-identity (for example, representing the presence of exon "A" on cDNA 1 wherein cDNA 2 contains exon "B" instead). Because the two cDNAs contain regions of sequence identity they will both hybridize to a probe derived from the entire gene or portions of the gene containing sequences found on both cDNAs; the two splice variants are therefore substantially homologous to such a probe and to each other.

The terms "in operable combination," "in operable order," and "operably linked" as used herein refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced.

The term "transgene" as used herein refers to a foreign gene that is placed into an organism by, for example, introducing the foreign gene into newly fertilized eggs or early embryos. The term "foreign gene" refers to any nucleic acid (e.g., gene sequence) that is introduced into the genome of an animal by experimental manipulations and may include gene sequences found in that animal so long as the introduced gene does not reside in the same location as does the naturally occurring gene.

As used herein, the term "vector" is used in reference to nucleic acid molecules that transfer DNA segment(s) from one cell to another. The term "vehicle" is sometimes used interchangeably with "vector." Vectors are often derived from plasmids, bacteriophages, or plant or animal viruses.

The term "expression vector" as used herein refers to a recombinant DNA molecule containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

The terms "overexpression" and "overexpressing" and grammatical equivalents, are used in reference to levels of mRNA to indicate a level of expression approximately 3-fold higher (or greater) than that observed in a given tissue in a control or non-transgenic animal. Levels of mRNA are measured using any of a number of techniques known to those skilled in the art including, but not limited to Northern blot analysis. Appropriate controls are included on the Northern blot to control for differences in the amount of RNA loaded from each tissue analyzed (e.g., the amount of 28S rRNA, an abundant RNA transcript present at essentially the same amount in all tissues, present in each sample can be used as a means of normalizing or standardizing the mRNA-specific signal observed on Northern blots). The amount of mRNA present in the band corresponding in size to the correctly spliced transgene RNA is quantified; other minor species of RNA which hybridize to the transgene probe are not considered in the quantification of the expression of the transgenic mRNA.

The term "transfection" as used herein refers to the introduction of foreign DNA into eukaryotic cells. Transfection may be accomplished by a variety of means known to the art including calcium phosphate-DNA co-precipitation, DEAE-dextran-mediated transfection, polybrene-mediated transfection, electroporation, microinjection, liposome fusion, lipofection, protoplast fusion, retroviral infection, and biolistics.

The term "calcium phosphate co-precipitation" refers to a technique for the introduction of nucleic acids into a cell. The uptake of nucleic acids by cells is enhanced when the nucleic acid is presented as a calcium phosphate-nucleic acid co-precipitate. The original technique of Graham and van der Eb (Graham and van der Eb, Virol., 52:456 [1973]), has been modified by several groups to optimize conditions for particular types of cells. The art is well aware of these numerous modifications.

The term "stable transfection" or "stably transfected" refers to the introduction and integration of foreign DNA into the genome of the transfected cell. The term "stable transfectant" refers to a cell that has stably integrated foreign DNA into the genomic DNA.

The term "transient transfection" or "transiently transfected" refers to the introduction of foreign DNA into a cell where the foreign DNA fails to integrate into the genome of the transfected cell. The foreign DNA persists in the nucleus of the transfected cell for several days. During this time the foreign DNA is subject to the regulatory controls that govern the expression of endogenous genes in the chromosomes. The term "transient transfectant" refers to cells that have taken up foreign DNA but have failed to integrate this DNA.

As used herein, the term "selectable marker" refers to the use of a gene that encodes an enzymatic activity that confers the ability to grow in medium lacking what would otherwise be an essential nutrient (e.g. the HIS3 gene in yeast cells); in addition, a selectable marker may confer resistance to an antibiotic or drug upon the cell in which the selectable marker is expressed. Selectable markers may be "dominant"; a dominant selectable marker encodes an enzymatic activity that can be detected in any eukaryotic cell line. Examples of dominant selectable markers include the bacterial aminoglycoside 3' phosphotransferase gene (also referred to as the neo gene) that confers resistance to the drug G418 in mammalian cells, the bacterial hygromycin G phosphotransferase (hyg) gene that confers resistance to the antibiotic hygromycin and the bacterial xanthine-guanine phosphoribosyl transferase gene (also referred to as the gpt gene) that confers the ability to grow in the presence of mycophenolic acid. Other selectable markers are not dominant in that their use must be in conjunction with a cell line that lacks the relevant enzyme activity. Examples of non-dominant selectable markers include the thymidine kinase (tk) gene that is used in conjunction with tk⁻ cell lines, the CAD gene that is used in conjunction with CAD-deficient cells and the mammalian hypoxanthine-guanine phosphoribosyl transferase (hprt) gene that is used in conjunction with hprt⁻ cell lines. A review of the use of selectable markers in mammalian cell lines is provided in Sambrook, J. et al., Molecular Cloning: A Laboratory Manual, 2nd ed., Cold Spring Harbor Laboratory Press, New York (1989) pp. 16.9-16.15.

As used herein, the term "cell culture" refers to any in vitro culture of cells. Included within this term are continuous cell lines (e.g., with an immortal phenotype), primary cell cultures, transformed cell lines, finite cell lines (e.g., non-transformed cells), and any other cell population maintained in vitro.

As used, the term "eukaryote" refers to organisms distinguishable from "prokaryotes." It is intended that the term encompass all organisms with cells that exhibit the usual characteristics of eukaryotes, such as the presence of a true nucleus bounded by a nuclear membrane, within which lie the chromosomes, the presence of membrane-bound organelles, and other characteristics commonly observed in eukaryotic organisms. Thus, the term includes, but is not limited to such organisms as fungi, protozoa, and animals (e.g., humans).

As used herein, the term "in vitro" refers to an artificial environment and to processes or reactions that occur within an artificial environment. In vitro environments can consist of, but are not limited to, test tubes and cell culture. The term "in vivo" refers to the natural environment (e.g., an animal or a cell) and to processes or reaction that occur within a natural environment.

The terms "test compound" and "candidate compound" refer to any chemical entity, pharmaceutical, drug, and the like that is a candidate for use to treat or prevent a disease, illness, sickness, or disorder of bodily function (e.g., cancer).

Test compounds comprise both known and potential therapeutic compounds. A test compound can be determined to be therapeutic by screening using the screening methods of the present invention. In some embodiments of the present invention, test compounds include antisense compounds.

As used herein, the term "sample" is used in its broadest sense. In one sense, it is meant to include a specimen or culture obtained from any source, as well as biological and environmental samples. Biological samples may be obtained from animals (including humans) and encompass fluids, solids, tissues, and gases. Biological samples include blood products, such as plasma, serum and the like. Environmental samples include environmental material such as surface matter, soil, water, crystals and industrial samples. Such examples are not however to be construed as limiting the sample types applicable to the present invention.

DETAILED DESCRIPTION OF THE INVENTION

The present invention relates to compositions and methods for the protection and restoration of hearing. In particular, the present invention relates to treatments to facilitate the protection and re-growth of the auditory nerve. The present invention further provides methods of preventing hair cell loss and the accompanying loss in hearing. The present invention contemplates a variety of treatments. Exemplary, non-limiting examples of each class of treatment are provided below. In some preferred embodiments, the treatments are provided in combination with one or more additional treatments. The present invention contemplates a variety of methods of delivering treatments to the ear including, but not limited to, those disclosed herein.

I. Treatments

In some embodiments, a single treatment is provided for the preservation and re-growth of the auditory nerve. A variety of treatments are described below. The present invention is not limited to the exemplary methods and compounds described below. The present invention is intended to encompass additional suitable compounds in each group. Methods for the screening of potential compounds include, but are not limited to, those disclosed herein (e.g., in Examples 1-3 below).

A. Continuous Stimulation

In some embodiments, the present invention provides methods comprising the administration of chronic (i.e., continuous) electrical stimulation (ES). Results obtained during the development of the present invention (Example 2) provided the novel result of regeneration of the auditory nerve following chronic stimulation.

The present invention is not limited to a particular mechanism. Indeed, an understanding of the mechanism is not necessary to practice the present invention. Nonetheless, it is contemplated that several pathways for protection resulting from depolarization are possible and one or more may be involved in the effects of ES in the cochlea. These pathways include 1) regulation of $Ca^{2+}$ via L-type voltage gated $Ca^{2+}$ channel, 2) an autocrine neurotrophin loop, 3) cAMP production, and 4) CAM kinase-mediated phosphorylation of CREB, with subsequent changes in gene expression (Gong et al., Neuroscience Letters 263:153 [1999]). In SGC cultures, depolarization elevates cAMP and result in SGC protection (Hartshorn et al., Otolaryngol Head Neck Surg., 104:311 [1991]). Electrical activity has been shown to elevate $Ca^{2+}$ concentration, leading to increase in intracellular elevation of cAMP resulting in neuronal extension (Ming et al., Neuron, 29:441 [2001]). SGC protection with ES is mediated by L-type voltage gated $Ca^{2+}$ channels in vitro (Hegarty et al., J. Neurosci., 17:1959 [1997]) and in vivo (Miller et al., Hear Res., 151:1 [2001]).

Accordingly, in some embodiments, the present invention provides treatment with ES, alone, or in combination (e.g., with neurotrophins), to improve the survival of SGCs of deaf individuals. Methods for the delivery of ES are provided in the below discussion and in illustrative Example 2.

B. Classic Neurotrophic Factors

In some embodiments, neurotrophic factors are utilized in the methods of the present invention. The present invention is not limited to a particular neurotrophic factor. Any neurotrophic factor that has the desired effect of protecting or promoting re-growth of the auditory nerve, alone or in combination, may be utilized including, but not limited to, glial cell line-derived neurotrophic factor, brain-derived neurotrophic factor, neurotrophin-3, neurotrophin-4/5, and ciliary neurotrophic factor.

In some preferred embodiments, glial cell line-derived neurotrophic factor (GDNF) is utilized in the methods of the present invention. GDNF and its receptors are expressed in the inner ear (Rathbone et al., Progress in Neurobiology 59:663 [1999]; Shepherd et al., Hear Res 66:108 [1993]). In addition, GDNF expression is upregulated with deafferentation (Miller et al., Current Opinion In Otolaryngology—Head and Neck Surgery, 6:301 [1998]). In some embodiments, neurotrophins are administered with one or more additional therapies (e.g., ES therapy). Illustrative Example 1 describes the protective effect of GDNF and ES combination treatment. Methods for the administration of neurotrophins to the ear include, but are not limited to, those described below.

C. Atypical Neurotrophic Factors

In other embodiments, the present invention contemplates the use of atypical neurotrophic factors including, but not limited to, purine and pyrimidine-based nucleoside and nucleotide analogs for the protection and regrowth of the auditory nerve. Purine-based compounds include nucleotides (e.g., including, but not limited to, adenosine triphosphate (ATP) and guanosine triphosphate (GTP)), nucleosides (e.g., adenosine, guanine), and purine bases (e.g., including, but not limited to, adenine, guanine).

Current uses of naturally occurring purine-based compounds include anti-asthmatic treatment with theophylline, use of adenosine in cardiology, and experimental applications of ATP in oncology. In addition, synthetic purine derivatives are now being examined clinically, including isoprinosine, an antiviral agent; AIT-082, a potential treatment in Alzheimer's disease (Rathbone et al., Progress in Neurobiology, 59:663 [1999]), as well as excitotoxicity/neurodegeneration (Di Iorio et al., Experimental Neurology, 169:392 [2001]); and propentofylline, which may also be an effective treatment in Alzheimer's patients. Recently, interest has focused on GTP, guanine, and related compounds (Rathbone et al., Progress in Neurobiology, 59:663 [1999]), including inosine, which drives an impressive degree of axonal sprouting, and potentially axonal regeneration, following corticospinal tract transection in rats (Di Iorio et al. Drug Dev. Res., 52:303 [2001]).

The present invention is not limited to a particular mechanism. Indeed, an understanding of the mechanism is not necessary to practice the present invention. Nonetheless, it is contemplated that purine and pyrimidine compounds have activities that include, but are not limited to, increased neuronal cell survival, proliferation, and neuronal sprouting (neuritogenesis), as well as increased neurotransmitter-mediated neural activity which will further contribute to cell survival. These effects may be mediated by the nucleotides via G protein-coupled P2Y receptors but also P2X receptors have recently been implicated in developmental roles.

The efficacy of a variety of combinations (purines and trophic factors) can be assayed using the in vitro system and in vivo methods described herein. For example, in vitro experiments (See e.g., Example 4) allow direct assessment of responsiveness of human spiral ganglion cells to these factors. Once an optimal combination is identified, testing is performed in animal models (See e.g., Example 1 and the below description of methods of administering treatments). In vivo, drug application is achieved e.g., by local delivery of both classes of compounds locally, or by systemic dietary administration of nucleotides or nucleosides, in combination with local growth factor delivery.

D. Antioxidants

In still further embodiments, the present invention utilizes antioxidants in the protection of the auditory nerve from degradation. Experiments conducted during the course of the development of the present invention (Example 3) demonstrated that systemic antioxidant treatment affects auditory nerve physiology, resulting in more sensitive electrically evoked potential threshold levels. Accordingly, the present invention provides methods of protecting the auditory nerve comprising the administration of antioxidants (e.g., including, but not limited to, trolox and ascorbic acid), alone or in combination with other treatments (e.g., including, but not limited to, those disclosed herein).

The present invention is not limited to the antioxidants disclosed herein. Any suitable antioxidant may be utilized in the methods and compositions of the present invention including, but not limited to, Iron chelators (e.g., including, but not limited to, Desferal, Deferiprone, Hydroxypyridone derived iron, N,N'-bis-dibenzylethylenediaminediacetic acid (DBED), Demethyl, Hydroxypyrid, Diethyl Hydroxypyrid-4-one, Ethyl Hydroxy Hydroxypyrid-4-on-1 y) propionic acid, Ethylene-1,-diamine); Thiol-antioxidants (e.g., including, but not limited to, Glutathione, Glutathione ethyl and isopropyl esters, Acetylcysteine, D-penicillamine, α-lipoic acid, metleyl-thio urea, d-methionine); Nitrone spin traps (e.g., including, but not limited to Phenyl-t-butyl nirone); Aminosteroids (e.g., including, but not limited to 21-aminosteroids (lazaroids)); Phenols and catechols (e.g., including, but not limited to α-tocopherol, melatonin, nitecapone, apomorphine, BHA, 4-Hydroxyestradiol, quercitin). Exemplary methods for the administration of antioxidants and screening for antioxidants with protective activity are described below and in illustrative Example 3.

E. Combination Treatments

In some preferred embodiments of the present invention, two or more of the above-described treatments are administered concurrently. For example, in some embodiments, ES and neurotrophins are administered concurrently. Experiments conducted during the development of the present invention (Example 1) demonstrated that co-administration of ES and GDNF resulted in an additive increase in the preservation of SGCs. The present invention is not limited to the combination of ES and GDNF. Indeed, any number of suitable combinations is contemplated by the present invention including, but not limited to, the combination of ES and other trophic (e.g., neurotrophins and purine or pyrimidine compounds) or antioxidant factors.

II. Delivery of Treatments

The present invention contemplates any suitable method of administering therapeutic compounds of the present invention. For example, in some embodiments, compounds are administered systemically. However, in preferred embodiments, treatments are delivered locally to the ear.

A. Systemic

In some embodiments, therapeutics are administered systemically. Preferred compounds for systemic administration are those that lack a wide distribution of receptors or those that do not have negative systemic effects. For example, in some embodiments, antioxidant therapy is delivered systemically.

B. Localized

In some preferred embodiments, compounds are directly infused into the cochlea. In some embodiments, compounds are administered via a cochleostomy created in the basal turn.

In some preferred embodiments, compounds are infused using a mini-osmotic pump (Brown et al., Hear Res., 70:167 [1993]; Prieskorn and Miller, Hearing Res., 140:212 [2000]). In some embodiments, a cannula system is utilized to provide access, via a hand-drilled cochleostomy, to the inner ear, while allowing periodic pump changes in order to enable changes in the drug being infused over time, and/or to prolong the interval of drug delivery. In some embodiments, the cannula allows direct (manual) injection into the cochlea, as accessed through the round window or via a cochleostomy (Stover et al., Hear Res., 136:124 [1999]), as well as round window placement of the cannula tip for the purposes of middle ear drug delivery. In addition, in some embodiments, the cannula design is modified to enable simultaneous intracochlear drug infusion and electrical stimulation via a cochlear implant.

In other embodiments, treatments are injected into the cochlea through a cochleostomy created in the basal turn via manual injection (Brown et al., Hear Res., 70:167 [1993]; Prieskorn and Miller Hear Res., 140:212 [2000]). In still further embodiments, treatments are administered via indirect infusion. This method takes advantage of the semi-permeable nature of the round window membrane to deliver small molecules into the middle ear space, from which they pass into the inner ear. In yet other embodiments, the treatment is incorporated into a biopolymer matrix on a cochlear implant, resulting in gradual, chronic release of the substance from along the implant's length within the cochlea. The present invention is not limited to the local delivery methods described herein. Any suitable method that delivers therapeutics to the inner ear may be utilized.

C. Gene Therapy

In some embodiments, treatments are delivered to the ear via gene therapy. The use of gene therapy involves the introduction of the gene into cells that then secrete the gene product. Gene therapy allows for the continuous production and secretion of the protein over a period of weeks and perhaps months. In some preferred embodiments, vectors for the delivery of the gene comprise a promoter that specifically directs gene expression in the ear, but not in other organs, thus providing local delivery of the gene of interest (See e.g., Cohen-Salmon et al., PNASE 94:14450 [1997]; Cohen-Salmon et al., Molecular Biology of Hearing and Deafness, Bethesda, Md. Oct. 4-7, [2001]; Ryan et al., Molecular Biology of Hearing and Deafness, Bethesda, Md. Oct. 4-7, [2001]).

Viral vectors commonly used for in vivo or ex vivo targeting and therapy procedures are DNA-based vectors and retroviral vectors. Methods for constructing and using viral vectors are known in the art (See e.g., Miller and Rosman, BioTech., 7:980-990 [1992]). Preferably, the viral vectors are replication defective, that is, they are unable to replicate autonomously in the target cell. In general, the genome of the replication defective viral vectors that are used within the scope of the present invention lack at least one region that is necessary for the replication of the virus in the infected cell. These regions can either be eliminated (in whole or in part), or be rendered non-functional by any technique known to a person skilled in the art. These techniques include the total removal, substitution (by other sequences, in particular by the inserted nucleic acid), partial deletion or addition of one or more bases to an essential (for replication) region. Such techniques may be performed in vitro (i.e., on the isolated DNA) or in situ, using the techniques of genetic manipulation or by treatment with mutagenic agents.

Preferably, the replication defective virus retains the sequences of its genome that are necessary for encapsidating the viral particles. DNA viral vectors include an attenuated or defective DNA viruses, including, but not limited to, herpes simplex virus (HSV), papillomavirus, Epstein Barr virus (EBV), adenovirus, adeno-associated virus (AAV), and the like. Defective viruses, that entirely or almost entirely lack viral genes, are preferred, as defective virus is not infective after introduction into a cell. Use of defective viral vectors allows for administration to cells in a specific, localized area, without concern that the vector can infect other cells. Thus, a specific tissue can be specifically targeted. Examples of particular vectors include, but are not limited to, a defective herpes virus 1 (HSV1) vector (Kaplitt et al., Mol. Cell. Neurosci., 2:320-330 [1991]), defective herpes virus vector lacking a glycoprotein L gene (See e.g., Patent Publication RD 371005 A), or other defective herpes virus vectors (See e.g., WO 94/21807; and WO 92/05263); an attenuated adenovirus vector, such as the vector described by Stratford-Perricaudet et al. (J. Clin. Invest., 90:626-630 [1992]; See also, La Salle et al., Science 259:988-990 [1993]); and a defective adeno-associated virus vector (Samulski et al., J. Virol., 61:3096-3101 [1987]; Samulski et al., J. Virol., 63:3822-3828 [1989]; and Lebkowski et al., Mol. Cell. Biol., 8:3988-3996 [1988]).

Preferably, for in vivo administration, an appropriate immunosuppressive treatment is employed in conjunction with the viral vector (e.g., adenovirus vector), to avoid immuno-deactivation of the viral vector and transfected cells. For example, immunosuppressive cytokines, such as interleukin-12 (IL-12), interferon-gamma (IFN-γ), or anti-CD4 antibody, can be administered to block humoral or cellular immune responses to the viral vectors. In addition, it is advantageous to employ a viral vector that is engineered to express a minimal number of antigens.

In a preferred embodiment, the vector is an adenovirus vector. Adenoviruses are eukaryotic DNA viruses that can be modified to efficiently deliver a nucleic acid of the invention to a variety of cell types. Various serotypes of adenovirus exist. Of these serotypes, preference is given, within the scope of the present invention, to type 2 or type 5 human adenoviruses (Ad 2 or Ad 5), or adenoviruses of animal origin (See e.g., WO 94/26914). Those adenoviruses of animal origin that can be used within the scope of the present invention include adenoviruses of canine, bovine, murine (e.g., Mav1, Beard et al., Virol., 75-81 [1990]), ovine, porcine, avian, and simian (e.g., SAV) origin. Preferably, the adenovirus of animal origin is a canine adenovirus, more preferably a CAV2 adenovirus (e.g. Manhattan or A26/61 strain (ATCC VR-800)).

Preferably, the replication defective adenoviral vectors of the invention comprise the ITRs, an encapsidation sequence and the nucleic acid of interest. Still more preferably, at least the E1 region of the adenoviral vector is non-functional. The deletion in the E1 region preferably extends from nucleotides 455 to 3329 in the sequence of the Ad5 adenovirus (PvuII-BglII fragment) or 382 to 3446 (HinfII-Sau3A fragment). Other regions may also be modified, in particular the E3 region (e.g., WO 95/02697), the E2 region (e.g., WO 94/28938), the E4 region (e.g., WO 94/28152, WO 94/12649 and WO 95/02697), or in any of the late genes L1-L5.

In a preferred embodiment, the adenoviral vector has a deletion in the E1 region (Ad 1.0). Examples of E1-deleted adenoviruses are disclosed in EP 185,573, the contents of which are incorporated herein by reference. In another preferred embodiment, the adenoviral vector has a deletion in the E1 and E4 regions (Ad 3.0). Examples of E1/E4-deleted adenoviruses are disclosed in WO 95/02697 and WO 96/22378. In still another preferred embodiment, the adenoviral vector has a deletion in the E1 region into which the E4 region and the nucleic acid sequence are inserted.

The replication defective recombinant adenoviruses according to the invention can be prepared by any technique known to the person skilled in the art (See e.g., Levrero et al., Gene 101:195 [1991]; EP 185 573; and Graham, EMBO J., 3:2917 [1984]). In particular, they can be prepared by homologous recombination between an adenovirus and a plasmid that carries, inter alia, the DNA sequence of interest. The homologous recombination is accomplished following co-transfection of the adenovirus and plasmid into an appropriate cell line. The cell line that is employed should preferably (i) be transformable by the elements to be used, and (ii) contain the sequences that are able to complement the part of the genome of the replication defective adenovirus, preferably in integrated form in order to avoid the risks of recombination. Examples of cell lines that may be used are the human embryonic kidney cell line 293 (Graham et al., J. Gen. Virol., 36:59 [1977]), which contains the left-hand portion of the genome of an Ad5 adenovirus (12%) integrated into its genome, and cell lines that are able to complement the E1 and E4 functions, as described in applications WO 94/26914 and WO 95/02697. Recombinant adenoviruses are recovered and purified using standard molecular biological techniques that are well known to one of ordinary skill in the art.

The adeno-associated viruses (AAV) are DNA viruses of relatively small size that can integrate, in a stable and site-specific manner, into the genome of the cells that they infect. They are able to infect a wide spectrum of cells without inducing any effects on cellular growth, morphology or differentiation, and they do not appear to be involved in human pathologies. The AAV genome has been cloned, sequenced and characterized. It encompasses approximately 4700 bases and contains an inverted terminal repeat (ITR) region of approximately 145 bases at each end, which serves as an origin of replication for the virus. The remainder of the genome is divided into two essential regions that carry the encapsidation functions: the left-hand part of the genome, that contains the rep gene involved in viral replication and expression of the viral genes; and the right-hand part of the genome, that contains the cap gene encoding the capsid proteins of the virus.

The use of vectors derived from the AAVs for transferring genes in vitro and in vivo has been described (See e.g., WO 91/18088; WO 93/09239; U.S. Pat. No. 4,797,368; U.S. Pat. No., 5,139,941; and EP 488 528, all of which are herein incorporated by reference). These publications describe various AAV-derived constructs in which the rep and/or cap genes are deleted and replaced by a gene of interest, and the use of these constructs for transferring the gene of interest in vitro (into cultured cells) or in vivo (directly into an organism). The replication defective recombinant AAVs according to the invention can be prepared by co-transfecting a plasmid containing the nucleic acid sequence of interest flanked by two AAV inverted terminal repeat (ITR) regions, and a plasmid carrying the AAV encapsidation genes (rep and cap genes), into a cell line that is infected with a human helper virus (for example an adenovirus). The AAV recombinants that are produced are then purified by standard techniques.

In another embodiment, the gene can be introduced in a retroviral vector (e.g., as described in U.S. Pat. Nos. 5,399,346, 4,650,764, 4,980,289 and 5,124,263; all of which are herein incorporated by reference; Mann et al., Cell 33:153 [1983]; Markowitz et al., J. Virol., 62:1120 [1988]; PCT/US95/14575; EP 453242; EP178220; Bernstein et al. Genet. Eng., 7:235 [1985]; McCormick, BioTechnol., 3:689 [1985]; WO 95/07358; and Kuo et al., Blood 82:845 [1993]). The retroviruses are integrating viruses that infect dividing cells. The retrovirus genome includes two LTRs, an encapsidation sequence and three coding regions (gag, pol and env). In recombinant retroviral vectors, the gag, pol and env genes are generally deleted, in whole or in part, and replaced with a heterologous nucleic acid sequence of interest. These vectors can be constructed from different types of retrovirus, such as, HIV, MoMuLV ("murine Moloney leukaemia virus" MSV ("murine Moloney sarcoma virus"), HaSV ("Harvey sarcoma virus"); SNV ("spleen necrosis virus"); RSV ("Rous sarcoma virus") and Friend virus. Defective retroviral vectors are also disclosed in WO 95/02697.

In general, in order to construct recombinant retroviruses containing a nucleic acid sequence, a plasmid is constructed that contains the LTRs, the encapsidation sequence and the coding sequence. This construct is used to transfect a packaging cell line, which cell line is able to supply in trans the retroviral functions that are deficient in the plasmid. In general, the packaging cell lines are thus able to express the gag, pol and env genes. Such packaging cell lines have been described in the prior art, in particular the cell line PA317 (U.S. Pat. No. 4,861,719, herein incorporated by reference), the PsiCRIP cell line (See, WO90/02806), and the GP+en-vAm-12 cell line (See, WO89/07150). In addition, the recombinant retroviral vectors can contain modifications within the LTRs for suppressing transcriptional activity as well as extensive encapsidation sequences that may include a part of the gag gene (Bender et al., J. Virol., 61:1639 [1987]). Recombinant retroviral vectors are purified by standard techniques known to those having ordinary skill in the art.

Alternatively, the vector can be introduced in vivo by lipofection. For the past decade, there has been increasing use of liposomes for encapsulation and transfection of nucleic acids in vitro. Synthetic cationic lipids designed to limit the difficulties and dangers encountered with liposome mediated transfection can be used to prepare liposomes for in vivo transfection of a gene encoding a marker (Felgner et. al., Proc. Natl. Acad. Sci. USA 84:7413-7417 [1987]; See also, Mackey, et al., Proc. Natl. Acad. Sci. USA 85:8027-8031 [1988]; Ulmer et al., Science 259:1745-1748 [1993]). The use of cationic lipids may promote encapsulation of negatively charged nucleic acids, and also promote fusion with negatively charged cell membranes (Felgner and Ringold, Science 337:387-388 [1989]). Particularly useful lipid compounds and compositions for transfer of nucleic acids are described in WO95/18863 and WO96/17823, and in U.S. Pat. No. 5,459,127, herein incorporated by reference.

Other molecules are also useful for facilitating transfection of a nucleic acid in vivo, such as a cationic oligopeptide (e.g., WO95/21931), peptides derived from DNA binding proteins (e.g., WO96/25508), or a cationic polymer (e.g., WO95/21931).

DNA vectors for gene therapy can be introduced into the desired host cells by methods known in the art, including but not limited to transfection, electroporation, microinjection, transduction, cell fusion, DEAE dextran, calcium phosphate precipitation, use of a gene gun, or use of a DNA vector transporter (See e.g., Wu et al., J. Biol. Chem., 267:963 [1992]; Wu and Wu, J. Biol. Chem., 263:14621 [1988]; and Williams et al., Proc. Natl. Acad. Sci. USA 88:2726 [1991]). Receptor-mediated DNA delivery approaches can also be used (Curiel et al., Hum. Gene Ther., 3:147 [1992]; and Wu and Wu, J. Biol. Chem., 262:4429 [1987]).

III. Prevention of Hair Cell Damage

In some embodiments, the present invention provides methods of protecting against hearing loss (e.g., induced by noise or chemical toxicity). A common theme across the various mechanisms of hearing loss is the loss of sensory hair cells, which act as the sensory receptors in the auditory periphery. Two of the best-characterized causes of hearing loss, pharmacological ototoxicity and noise-induced hearing loss, are both associated with loss of hair cells (HC), followed by degenerative changes within the auditory nerve. Age-related changes in the auditory system include not only a primary loss of HC and auditory nerve fibers (White et al., Hear Res., 141:12 [2000]), but also downregulatory changes that increase the susceptibility of the auditory system to the effects of insults like noise and ototoxic drugs (Miller et al., Scandinavian Audiology Supplementum 48:53 [1998]). Consequently, it is contemplated that interventions directed at protective HC from damage are expected to not only reduce the incidence of noise- and drug-induced hearing loss, but also to decrease the severity of age-related hearing loss.

In some embodiments, antioxidants (e.g., including, but not limited to, those described herein) are utilized to protect hair cells. As in other subdivisions of the nervous system, recent evidence suggests that in the auditory system, there is a great deal of convergence in the pathways and cascades involved in cell death, regardless of the initial triggering event or insult. In particular, the generation of reactive oxygen species (ROS) is a common theme in HC death due to noise and ototoxic drugs (Kopke et al., Annals of the New York Academy of Sciences 884:171 [1999]). The effects of ROS are believed to include not only the direct toxic effects intrinsic to these highly reactive species, but also involve additional biochemical and physiological changes triggered by ROS, such as changes in cochlear blood flow (CBF) stimulated by isoprostanes (see Example 5). The experiments described in Example 7 demonstrated that an antioxidant (N-acetylcysteine) was successful in preventing hair cell loss. The experiments described in Example 5 demonstrated that administration of an antioxidant was able to protect against isoprostane-induced decreases in cochlear blood flow.

In other further embodiments, the up-regulation of heat shock proteins (HSP) is utilized to prevent hair cell loss and protect hearing. The experiments described in Example 6 indicate that temporary threshold shift from exposure to loud noise can be significantly reduced by a prior manipulation that results in the upregulation of expression of heat shock proteins. The data indicate that the expression of these proteins also can enhance recovery from a noise-induced hearing loss.

The present invention is not limited to a particular mechanism. Indeed, an understanding of the mechanism is not necessary to practice the present invention. Nonetheless, it is contemplated that exogenous interventions that further upregulate HSP may be effective in HC protection. Similarly, changes in CBF have been observed following noise exposure (See e.g., Quirk et al., Hear Res., 52:217 [1991]; Scheibe et al., European Archives of Oto-Rhino-Laryngology 250:281

[1993]). These changes, which presumably reflect at least in part the effects of lipid peroxidation products, isoprostanes, on the cochlear vasculature, may play a significant role in the subsequent pathological changes within the cell. Consequently, it is contemplated that interventions that affect the CBF, returning local perfusion to a more normal pattern, may be effective in protecting HC from noise or ototoxic trauma.

In additional embodiments, neurotrophic factors (e.g., including, but not limited to, those disclosed herein) are utilized to protect hair cells. In still further embodiments, NMDA receptor antagonists are utilized to protect hair cells. Experiments conducted during the course of development of the present invention demonstrated that an NMDA receptor antagonist (MK801) was successful in preventing hair cell loss (Example 7). In some embodiments, one or more of the treatments described herein are co-administered to prevent hair cell loss. Any combination that results in the desired effect (e.g., prevention of hair cell loss and the accompanying hearing loss) may be utilized.

EXPERIMENTAL

The following examples are provided in order to demonstrate and further illustrate certain preferred embodiments and aspects of the present invention and are not to be construed as limiting the scope thereof.

In the experimental disclosure which follows, the following abbreviations apply: N (normal); M (molar); mM (millimolar); µM (micromolar); mol (moles); mmol (millimoles); µmol (micromoles); nmol (nanomoles); pmol (picomoles); g (grams); mg (milligrams); µg (micrograms); ng (nanograms); l or L (liters); ml (milliliters); µl (microliters); cm (centimeters); mm (millimeters); µm (micrometers); nm (nanometers); and ° C. (degrees Centigrade).

Example 1

Protection of Spiral Ganglion Neurons GDNF Gene Therapy and Electrical Stimulation This Example describes the cumulative effect of the GDNF transgene delivered by adenoviral vectors (Ad-GDNF) and ES on the spiral ganglion cells (SGCs) after aminoglycoside/diuretic-induced ototoxicity that eliminated the inner hair cells.

A. Methods

Animals

Twenty-four pigmented guinea pigs (240-380 g) were used in this study. Animals were outbred in the Elm Hill supplier colony. All animal experiments were approved by the University Committee for the Use and Care of Animals and were performed using accepted veterinary standards. The University of Michigan is fully accredited by the Association for Assessment and Accreditation of Laboratory Animal Care International (AAA-LAC International).

General Experimental Paradigm and Experimental Groups

Animals were divided into three treatment groups: ES alone (N=7), GDNF transgene delivered by adenoviral vectors (Ad-GDNF) alone (N=7) or ES+Ad-GDNF combined (N=8). The implant and the Ad-GDNF were placed in the left ear, whereas the right ear served as a control. In addition, two normal (non-deafened) guinea pigs were used in the immunocytochemistry experiments to detect GDNF in the cochlea. Ad-GDNF was administered in these animals as in the Ad-GDNF alone experimental group.

On day 1, a combination of ototoxic drugs was systemically infused in order to eliminate most cochlear IHCs and OHCs bilaterally. On day 5, deafening was verified with acoustically-evoked auditory brainstem response audiometry (ABRs), and then aseptic surgery was performed to place a cochlear implant in the inner ear and/or inoculate the cochlea with adenovirus vector containing the human GDNF insert (Ad-GDNF). The recombinant adenovirus vector has been previously described (Lapchak et al., Brain Res., 777:153 [1997]). In animals that received ES, the stimulation started on day 8 following a baseline electrical ABR (eABR), to assure electrode function, and continued for 36 days. All animals were euthanized on day 44 following eABR measurement to reconfirm electrode function.

Acoustic Auditory Brainstem Responses (aABR)

Baseline and post-deafening (day 5) aABRs were performed on all subjects. Animals were anesthetized with xylazine (10 mg/kg IM) and ketamine HCL (40 mg/kg IM) and placed in a soundproof room. Neural responses were recorded with subcutaneous recording needle electrodes placed at the vertex (active) against a reference placed at the midline of the skull approximately 2 cm anterior to bregma, and in the thigh (ground). Computer-generated alternating polarity pulses (100 µsec duration, 50 pps) were delivered to a transducer positioned in the ear canal. Clicks were calibrated with Bruel and Kjaer ½" condenser microphone relative to SPL peak-to-peak equivalent. Stimulus-locked electrophysiological activity was averaged for 1,024 samples for 7.7 msec following stimulation. Stimuli were provided at various intensities to determine threshold, which was defined as the lowest stimulus intensity that evoked at least a 0.2 µV (peak to peak, with a latency of 1.6 to 3.2 msec) replicable waveform as previously described (Mitchell et al., Hear Res., 105:30 [1997]). Animals included in the study were required to have a baseline auditory ABR threshold equal to or less than 50 dB, and a post-deafening ABR threshold shift equal to or greater than 60 dB SPL.

Electrically Evoked Auditory Brain Stem Responses (eABR)

Animals with electrodes were anesthetized for eABRs on study days 8 and 44. Neural responses were recorded from epidural recording screws positioned at vertex (active), midline (reference) and ipsilateral to implant (ground). Two thousand forty-eight responses to 50 µS computer-generated monophasic current pulses, presented at 50 pulses/second with an alternating polarity on each presentation were averaged and analyzed in 5 dB steps near threshold. Threshold was determined by visual inspection of the responses and defined as the lowest intensity level at which a clear replicable waveform was visible in the evoked trace. For inclusion in this study subjects were required to demonstrate thresholds of less than 100 µA at the beginning and end of the stimulation period.

Deafening Procedure

On day 1 of the study, animals were injected with a single dose of kanamycin (400 mg/kg SC). Two hours later, animals were anesthetized as above and were prepared for cannulation of the jugular vein, as previously described (West et al., Arch. Otolaryngol., 98:32 [1973]), and infused with ethacrynic acid (40 or 50 mg/kg IV).

Adenoviral Vectors

A replication-deficient recombinant adenoviruses based on the human adenovirus serotype 5 in which three transcriptional regions (E1A and E1B and a portion of the E3) have been deleted (Lapchak et al., [1997], supra) was utilized. The vector contained the human GDNF gene driven by the cytomegalovirus (CMV) immediate promoter. Viral suspensions in 10% glycerol were kept at −80° C. until thawed for use.

Viral Administration and/or Electrode Implant Procedure

On day 5, animals were anesthetized with ketamine and xylazine as described above. In addition, chloramphenicol sodium succinate (30 mg/kg IN) was administered as a prophylactic antibiotic, and 0.5 ml of 1% lidocaine HCl was injected subcutaneously for local anesthesia. The middle ear was exposed via the postauricular approach. Under an operating microscope, a small fenestra was made with a sharp probe in the otic capsule at the base of the cochlea. In the group that received Ad-GDNF, a 100 µl Hamilton syringe attached to a vinyl cannula with a fine polyimide tip was used to slowly inject 5 µl of an isotonic adenoviral suspension (approximate concentration of $10^{10}$ adenoviral particles per milliliter in sterile normal Ringer's solution) into the scala tympani, as previously described (Stöver et al., Hear Res., 136:124 [1999]). Ten minutes after the inoculation the cannula was removed and the fenestra was covered with a small piece of fascia that adhered to the otic capsule. The bulla defect was sealed with carboxylate cement (DURELON, ESPE America, Norristown, Pa.). DEXON adsorbable suture was used for the subcuticular closure and the skin was closed with nylon sutures.

With respect to cochlear implants, prior to implantation, each stimulating electrode surface was activated to a stable minimal impedance value (2-5 kOhms) using cyclic voltometry (−0.9 to 0.5 v), for 30 min at 3 Hz (triangular wave) in saline. Epidural recording electrodes were placed at the vertex (1 cm posterior to bregma), mid-line (2 cm anterior to bregma) and ipsilateral parietal bone (1 cm lateral to bregma). A restraint bolt (to secure the portable stimulator) was fastened over bregma by 3 self-tapping screws. Methyl methacrylate was used to cement the recording electrodes, restraint bolt and electrode base to the skull. Animals were implanted via the postauricular approach described above, with a single ball (250 µm in diameter) electrode constructed from 90% platinum 10% iridium (Pt—Ir) wire (76 µm in diameter) inserted approximately 2 mm into scala tympani through the round window membrane. In addition to the stimulating electrode, an uninsulated 130 µm diameter Pt—Ir return electrode was placed in the middle ear. The ear was closed as above. In the group of animals that received both Ad-GDNF and ES, the virus was injected first, followed by electrode implantation. To prevent leakage of inner ear fluid and viral suspension, the round window membrane was covered with fascia.

Electrical Stimulation

On day 8, following eABR assessment, all implanted animals began continuous pulsatile ES via a wearable stimulator that was plugged into the electrode connector. The construction and performance details of this stimulator, custom made at the Kresge Hearing Research Institute, were previously described (Mitchell et al., Hear Res., 105:30 [1997]). Continuous stimulation (100 µA peak, 100 µsec/phase, 250 Hz) was provided for 36 days at a 40% duty cycle (400 µs on, 600 µs off). This value was empirically selected to represent a typical on time for an average implant user (Mitchell et al., [1997], supra).

Tissue Processing and Cell Counting

Forty-three days after deafening, following eABR measurement, the animals were deeply anesthetized, perfused intracardially with 2.5% glutaraldehyde, and decapitated. The temporal bones were removed for histological evaluation. Tissues were post-fixed in the same fixative for 2-3 hours. Cochlear tissues were decalcified in 4% EDTA with 0.25% glutaraldehyde for 2 days. Tissues were then dehydrated in a series of increasing ethanol concentrations, and embedded in JB-4 (Electron Microscopy Scientific, Washington, Pa.). Sections were obtained at a near mid-modiolar plane (1 µm thickness). Every 30th section was collected on a glass slide, stained with Paragon, and cover-slipped with Permount (Fisher Scientific, Pittsburgh, Pa.).

A total of 10 sections were collected for each cochlea. Among these 10, five slides were chosen randomly for counting and statistical analysis. If a low-quality (folds in the plastic) section was among those selected, it was replaced by another randomly selected section. In the guinea pig cochlea, mid-modiolar sections include seven regions of Rosenthal's canal. Frequently the upper Rosenthal's canals are inseparable. Thus, we assessed the number of SGCs in six regions (lower and upper basal, lower and upper second, lower and upper third turns). All neurons with a discernable nucleus present in the section were counted. SGC density (SGC number/10,000 $\mu m^2$) was calculated using Meta-Morph computerized image analysis system (Yagi et al., JARO, 4:315 [2001]). The entire area of Rosenthal's canal in each counted section was circled for the purpose of area calculation (performed by the software). The boundaries of the canal were drawn at the interface between the bone and the soft tissue within Rosenthal's canal. After counting the five sections of each cochlea, the average value of the SGC density was calculated for each cochlea. SGC density was analyzed using repeated measures ANOVA and post hoc paired comparisons made with Newman-Keuls multiple comparisons test. An unpaired Student's t test was used to evaluate statistical significance of difference between the right and left ears of each of the groups. A level of $P<0.05$ was considered significant.

Immunohistochemistry

To test the expression of the Ad-GDNF and its ability to synthesize GDNF in the cochlea, immunocytochemistry was performed using frozen specimens and GDNF-specific antibodies on two normal animals inoculated with Ad-GDNF. Guinea pigs were deeply anesthetized and perfused with 4% paraformaldehyde in phosphate buffer (PBS) through the aorta. After removal of the temporal bones, inner ear tissues were immersed in fixative for one hour. The specimens were decalcified in 4% EDTA in PBS for one week, then immersed in 30% sucrose (in PBS) overnight. Samples were then placed in vacuum for 30 min for embedding in OCT, and frozen in ethanol and dry ice, as previously described (Whitlon et al., Brain Res. Brain Res. Protoc., 6:159 [2001]). The frozen tissue blocks were sectioned at of 10 µm using a Leica CM3000 cryostat. Sections were air-dried for 2 hours, permeabilized in 0.3% Triton X-100 for 10 minutes, and then incubated in a polyclonal anti-GDNF antibody (Santa Cruz Biotechnology Inc. Santa Cruz, Calif.) for 60 minutes, rinsed in buffer and incubated with rhodamine conjugated goat-anti-rabbit secondary antibody (Jackson Immunoresearch Laboratories, Inc. West Grove, Pa.) diluted in 1:100 for 30 minutes. Following a final rinse, sections were mounted on microscope slides with Crystal/Mount. The negative control was the right side (not inoculated with the Ad-GDNF). Samples were analyzed and photographed with a Leica DMRB epifluorescence microscope.

B. Results

GDNF Over-Expression in Ad-GDNF Treated Ears

To determine the efficacy of Ad-GDNF inoculation mediated GDNF expression in the cochlea, vector-treated ears and control ears were prepared for immunocytochemistry with GDNF-specific antibodies. In inoculated ears the mesothelial cells demonstrated strong positive immunofluorescence. SGCs were also positive for the GDNF antibody in the inoculated ear, whereas in control ears the level of staining in these cells was much lower. SGCs and mesothelial cells in higher cochlear turns were also immunoreactive with the GDNF antibody.

Elimination of Hair Cells

In order to mimic sensorineural deafness caused by degeneration of IHCs, it is necessary to eliminate these cells. A combination of kanamycin with EA as previously described was used to eliminate IHCs. To qualify for inclusion in the study, animals had to have threshold shift from normal baseline greater than 60 dB measured by click-ABR. The cochlea of such animals typically has no surviving IHCs in the lower three turns. Occasional surviving IHC is seen in the apical turn, which was not used in counts for this study.

eABRs eABR results demonstrated that the implants were functional in all subjects receiving ES. All animals had an eABR threshold of less than 100 µA throughout the study. There was no significant difference in average eABR threshold between the ES and GDNF+ES groups. On average, eABR thresholds decreased over the course of the study by approximately 10% (Table 1).

SGC Survival in the ES Group

The influence of chronic ES on survival of SGC is illustrated in FIG. 1. Across the cochlear turns the density of SGC in the treated ear was larger than in the non-treated ear. This difference across the cochlea was significant at the $p<0.05$ level. For the basal turn (A and B) the difference between treated and non-treated ear was significant and, for the individual half turn, the upper basal region was significantly different in the treated vs. non-treated ear. The restricted effect of ES to the region of the electrode (first turn) is consistent with the restricted spread of current expected at this stimulation level and observed in previous studies (Mitchell et al., [1997], supra; Leake et al., Hear Res., 64:99 [1992]).

SGC Survival in the GDNF Group

Figure 2:
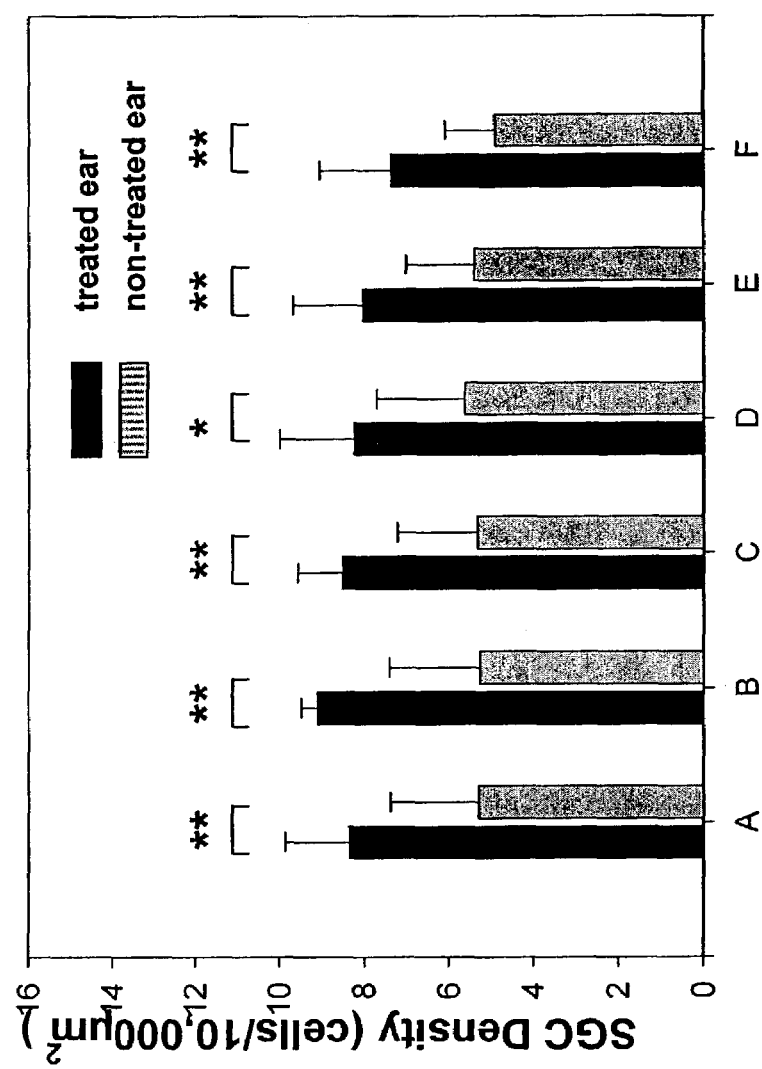
FIG. 2 shows a comparison between the density of SGCs in the treated versus the non-treated ears in the GDNF group (mean±SD). The density of surviving SGCs in treated and non-treated ears is shown in each one of the areas (A-F) analyzed.

Ears inoculated with Ad-GDNF exhibit robust protection of the treated (left) ears compared to the control (right) ears. The protective influence of GDNF was significant ($p<0.05$) in all cochlear turns (FIG. 2). While the protective effect was observed throughout the length of the cochlea, it was somewhat greater in the base, which is consistent with the previous finding of the density of distribution of viral vectors (Stöver et al., Hear Res., 136:124 [1999]).

SGC Survival in the Combined GDNF+ES Group

Figure 3:
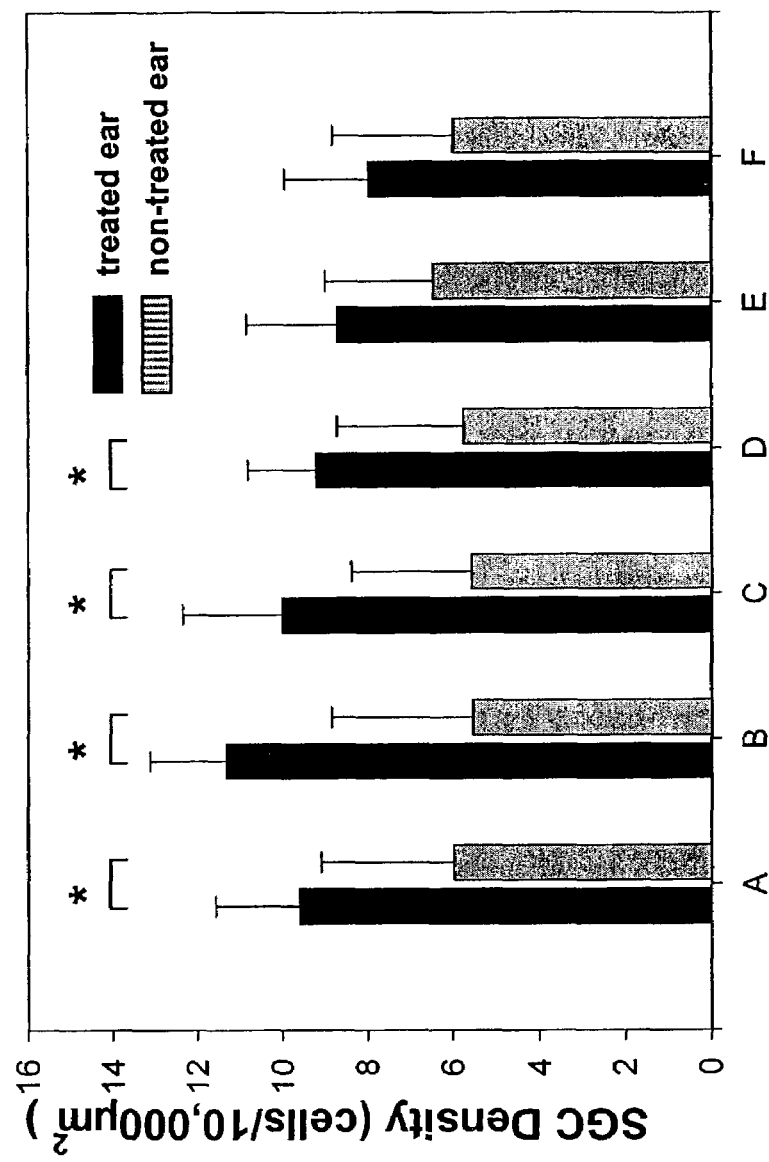
FIG. 3 shows a comparison between the density of SGCs in the treated and non-treated ears of the group receiving combined GDNF/ES (mean±SD).

In animals that received a combination of ES and GDNF, the SGC survival of was significantly greater ($p<0.05$) in treated versus control ears throughout the basal-most 2 turns of the cochlea (FIG. 3). While the difference was not significant ($p<0.05$) in the apical turn (areas E-F), a clear tendency for enhanced survival was observed.

Comparison Across Groups

Figure 4:
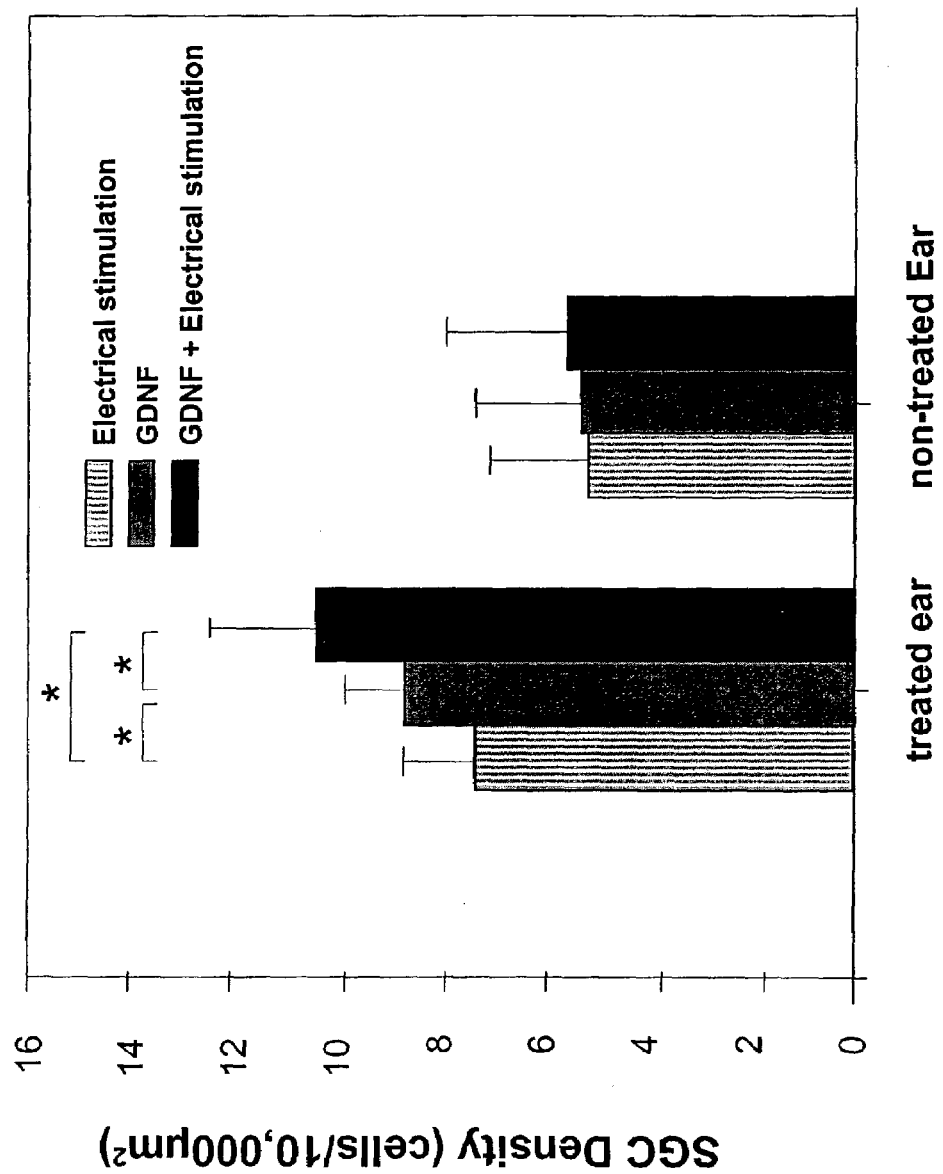
FIG. 4 shows a histogram comparing SGC density in ES, GDNF and GDNF/ES treated animals. The Figure shows the mean±SD (error bars).
Figure 5:
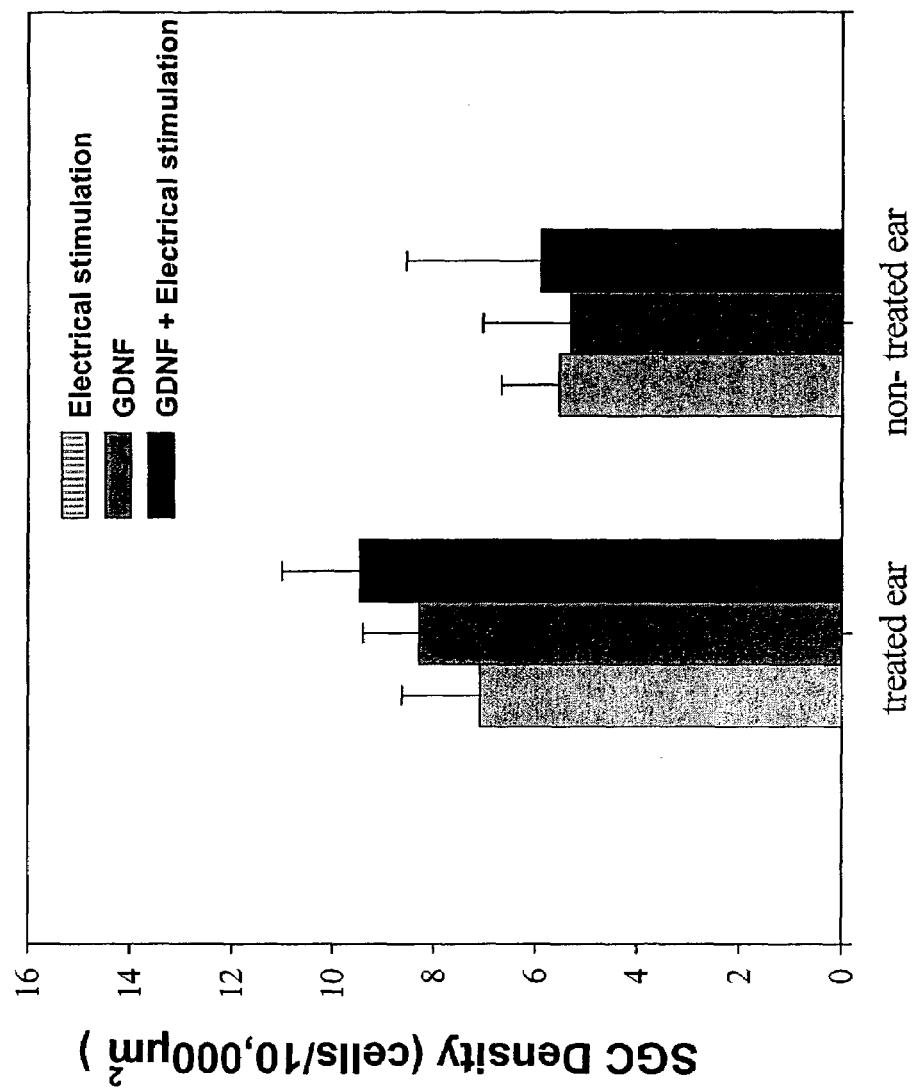
FIG. 5 shows a histogram comparing SGC density in ES, GDNF and GDNF/ES treated animals. The Figure shows the mean±SD (error bars).

Given the expected and observed restricted effect of ES on nerve survival, in analysis of the relative effectiveness of these agents, comparisons were restricted to the basal turn (region A and B) across these groups. FIG. 4 shows the SCC density of the basal turn for ears treated with ES alone, GDNF alone, or GDNF+ES, and their contralateral non-treated ears. Across the non-treated ears of these groups there was little difference. The difference between the treated and non-treated (control) ears of each group was significant at the $p<0.05$ level. The effectiveness of each treatment was significantly different ($p<0.05$), with GDNF+ES significantly more effective than either factor alone, and GDNF alone significantly more effective than ES alone. The density of SGCs in the upper basal turn versus upper and lower basal turns (combined) is summarized in Table 2. SGC density in the upper basal turn (region B) is higher than that in the lower basal turn (region A) in treated ears. The difference in density between GDNF+ES and ES in region B is small. In the lower three turns there were no significant differences in SGC density among the three groups (FIG. 5).

SG Morphology in all Groups

In cross-sections of the cochlea that are used for counting it is also possible to evaluate the general morphological features of the SGC. The best preservation of number and morphological features of the neurons was seen in the combined treated group. SGCs in control (deafened and non-treated) ears appeared shrunken, and the spaces between cells in Rosenthal's canal was larger than normal in control ears. SGCs in treated groups appeared to have a larger diameter than the control cells. There were smaller spaces between cells in the treated groups. The combined treatment group exhibited the largest cell size among the different groups in this study. No differences in nuclear morphology were noted among the four groups. In animals that received GDNF treatment the myelin was more prominent, allowing the distinction of nerve fibers.

This example demonstrated that GDNF and ES provided significantly better preservation of SGC density than either single treatment. The protective effects of Ad-GDNF+ES on denervated auditory neurons were additive.

TABLE 1

| | Mean eABR | |
|---|---|---|
| Treatment | Day 8 | Day 44 |
| GDNF/ES | 53 (±22.0) | 49.4 (±13.8) |
| ES | 59.3 (±15.4) | 52.1 (±10.8) |

TABLE 2

| | Mean SGC Density of Basal Turn | | | |
|---|---|---|---|---|
| Treatment | UB/Treated | UB/Non-Treated | UB + LB/Treated | UB + LB/Non-Treated |
| GDNF/ES | 11.3 (±1.8) | 5.7 (±2.9) | 10.5 (±2.0) | 5.6 (±2.4) |
| GDNF | 9.1 (±0.4) | 5.3 (±2.3) | 8.7 (±1.1) | 5.3 (±2.0) |
| ES | 7.4 (±1.4) | 5.3 (±2.0) | 7.2 (±1.5) | 5.1 (±1.9) |

Example 2

Regrowth of Auditory Nerve Peripheral Processes with Chronic Cochlear Electrical Stimulation This example describes the regrowth of peripheral process under chronic cochlear electrical stimulation.

Guinea pigs (Elm Hill) received baseline click evoked auditory brain stem response (ABR) measures and were then (day 0) bilaterally deafened with systemic kanamycin (400 mg/kg SQ) & ethacrynic acid (40 mg/kg IV). Following ABR to confirm a greater than 60 dB threshold shift (on day 4) a 3-T single ball electrode was inserted into scala tympani through the round window. The 5-T ground terminated in the bulla.

Beginning on day 7 and continuing for 2 weeks, experimental subjects (n=7) received continuous pulsatile, biphasic, charge balanced electrical stimulation from a battery powered, wearable stimulator. Stimuli were provided at a 40% duty cycle. EABR P1 thresholds were monitored to assure electrode function. The control group (n=6) were implanted but not stimulated. At day 21, following EABR, device position was confirmed, followed by systemic perfusion with 4% paraformaldehyde fixative, under heavy anesthesia. The otic capsule, lateral wall and Reissners and tectorial membranes were removed. The remaining portion of each cochlea was processed for immunoperoxidase staining with pan-trk antibody (to immunostain peripheral processes). Cochleae were then decalcified, embedded in plastic and sectioned in a paramodiolar plane. Sections were assessed for immunolabeled peripheral processes in the region formerly occupied by the organ of Corti and for myelinated fibers running in Rosenthal's canal to the habenula perforata.

The mean EABR threshold was 75 dB at day 7 and 53 dB at day 21, assuring electrode function in all stimulated animals. Pan-trk immunolabeling provides a specific marker for SGC processes. Using this marker, immunostained processes were seen in the electrically stimulated cochleae, in all turns of the cochlear spiral. Processes were most apparent in the former inner hair region but also seen in the former outer hair cell region. Chronic electrical stimulation increased the number of myelinated peripheral processes within Rosenthal's canal and the unmyelinated peripheral processes past the habenula, into the scar tissue of the region formerly occupied by the organ of Corti. Complete loss of this latter category (unmyelinated peripheral processes past the habenula) generally occurs by 4-5 days following deafening. Thus, it is likely that there was regrowth under conditions of chronic electrical stimulation.

Example 3

Effect of Systemic Treatment with Antioxidant on Auditory Function in Deafened Guinea Pigs This Example describes the effect of treatment with systemic antioxidants on deafened guinea pigs. Twenty-four guinea pigs were divided into 3 groups of 8 each. All subjects underwent aseptic surgery to implant an intracochlear Pt—Ir stimulating electrode, epidural recording electrodes and intracochlear cannula. Two groups were deafened by intracochlear infusion of 10% neomycin for 2 days (mini-osmotic pump model 2002, Alzet, Palo Alto, Calif., USA, flow rate: 0.5 µl/hr). The third normal hearing, control group received intracochlear artificial perilymph. Following deafening 8 animals received daily IP injections of trolox (10 mg/kg) and ascorbic acid (200 mg/kg) for 4 weeks. Deafened-untreated and hearing-control groups were injected with the same volume of saline for 4 weeks. Electrically evoked auditory brainstem responses, eABRs, were recorded on day 5, 9, 16, 23, 30, 37 and 44.

Figure 6:
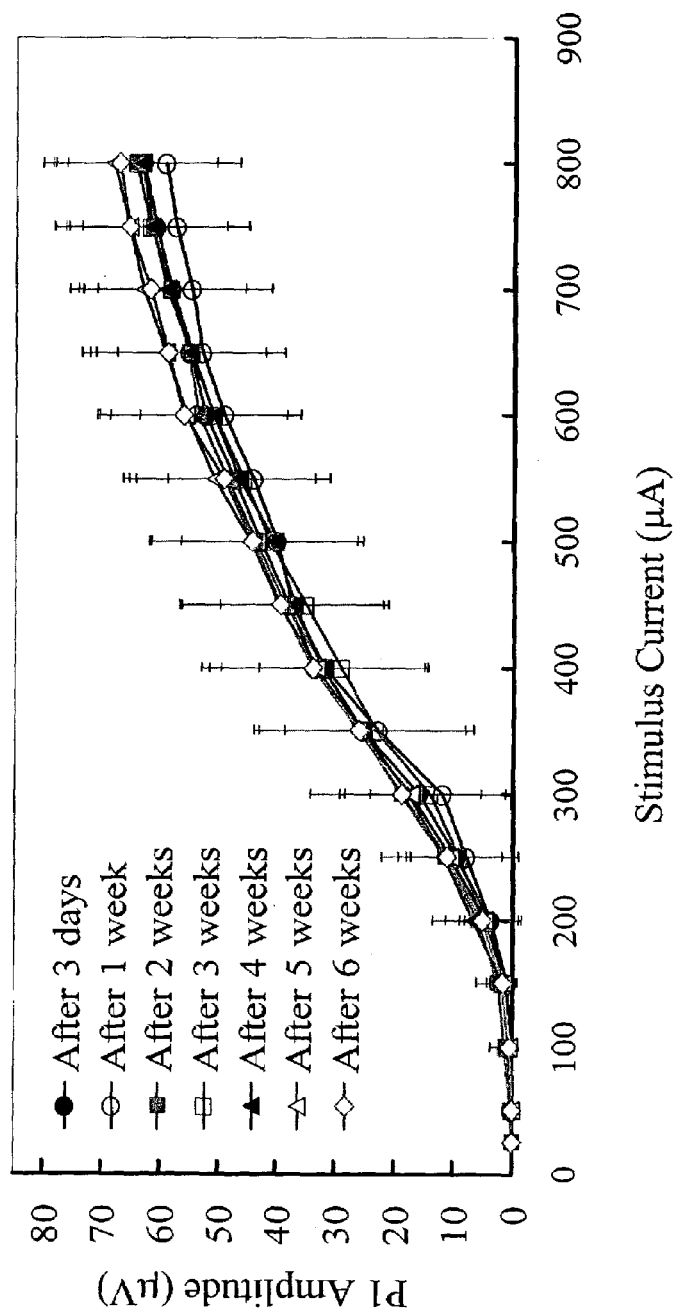
FIG. 6 shows P-1 amplitude for control animals.
Figure 7:
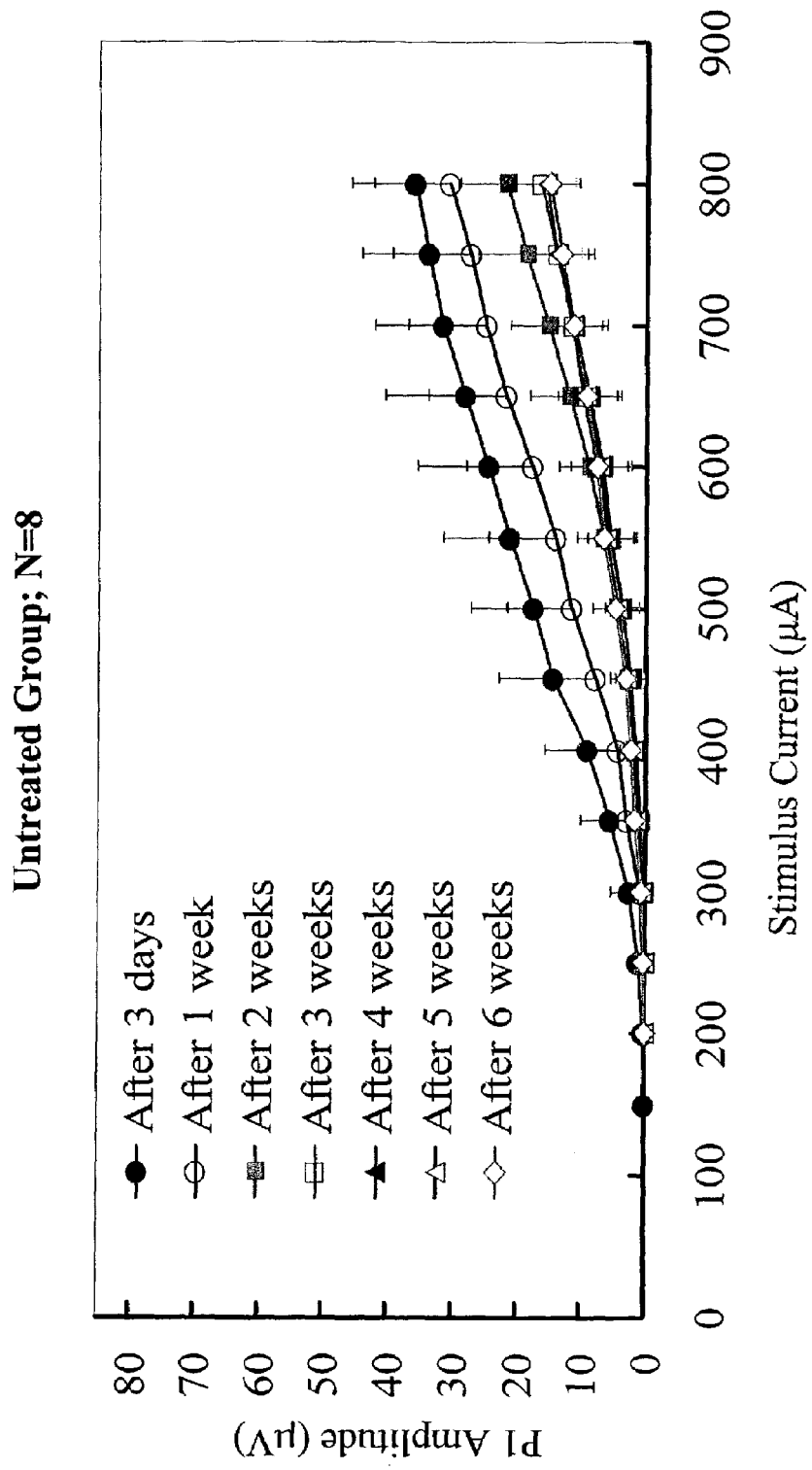
FIG. 7 shows P-1 amplitude for untreated animals.
Figure 8:
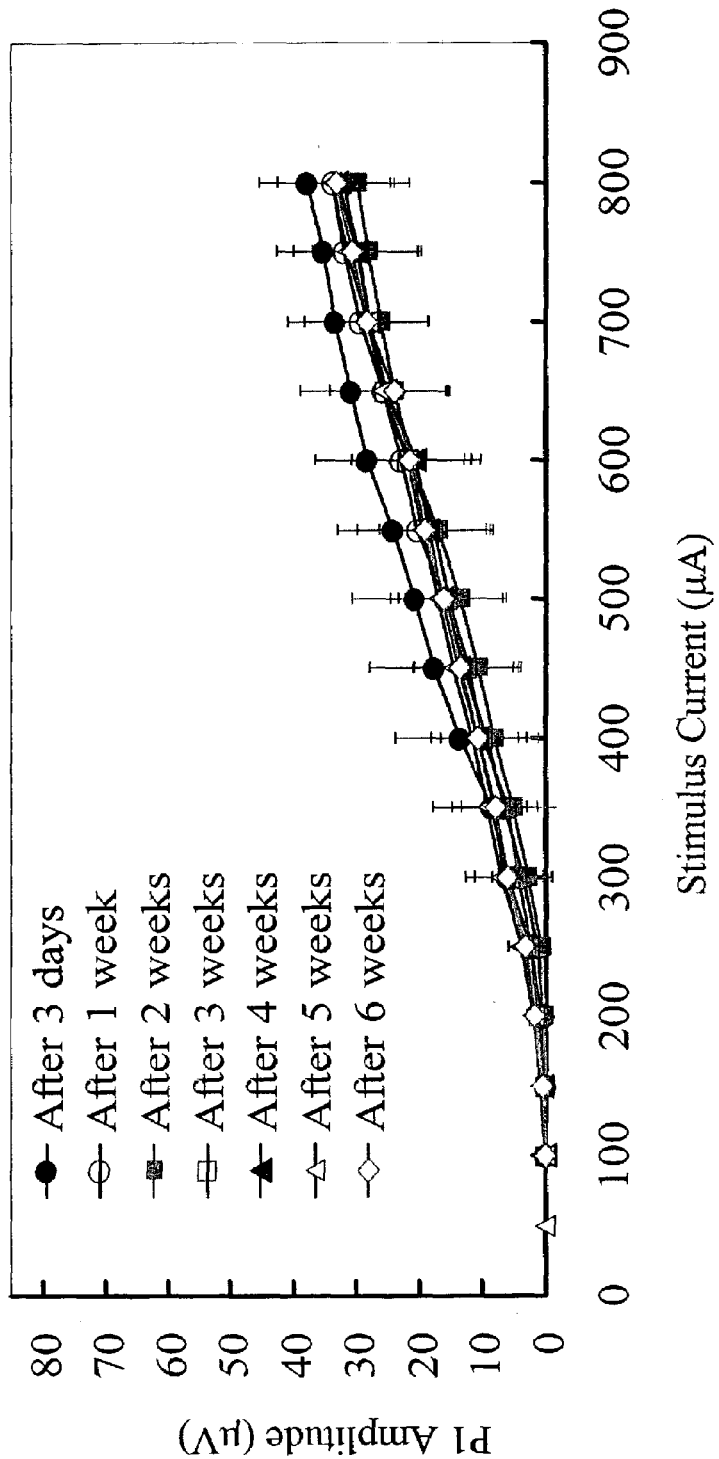
FIG. 8 shows P-1 amplitude for antioxidant treated animals.
Figure 9:
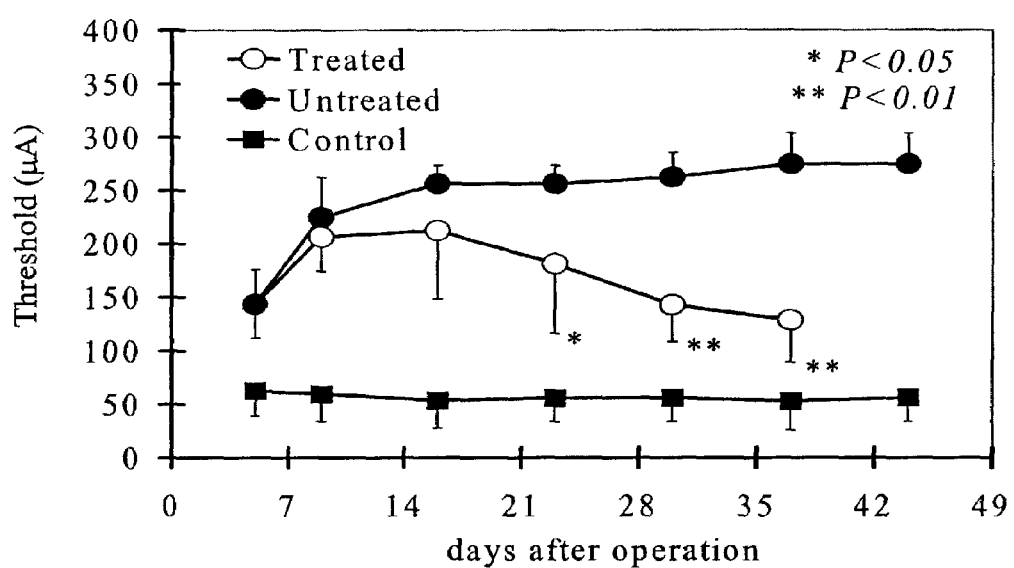
FIG. 9 describes eABR thresholds of deaf animals with and without antioxidant treatment.

The results are shown in FIGS. 6-9. FIG. 6 shows P-1 amplitude for the control group of animals. FIG. 7 shows P-1 amplitude for the untreated group. FIG. 8 shows P-1 amplitude for the antioxidant treated group. FIG. 9 shows eABR thresholds in treated, untreated, and control animals. In both deafened treated and untreated animals, eABR thresholds increased during the first 16 days, compared to undeafened controls. The eABR thresholds of antioxidant treated subjects decreased 3 weeks after start of treatment, while those of untreated group remained elevated. There were statistical significant differences between these two groups on day 23, 30, 37 and 44. The results indicate that systemic treatment with antioxidants increased electrical sensitivity of the deafferented auditory nerve.

Example 4

In Vitro Growth of Human Auditory Neurons

This example describes the development of techniques for culturing human spiral ganglion cells (SGCs) in vitro and assessing the influence of neurotrophins on their survival and growth. SGCs were obtained during petro-clival meningioma surgery. The expression of neurotrophin receptors in human SGCs was assessed with immunohistological studies.

During transcochlear approach to remove large life-threatening petro-clival menigioma, the facial nerve was exposed entirely and re-routed postero-inferiorly. The cochlea was dissected out using cutting and diamond drill leaving a thin bony capsule around it. The entire cochlea was taken out and placed immediately in culture medium. It was then transferred to the research laboratory and divided with a thin leaf-saw in the midmodiolar area. The small portion of nerve fibers in the cochlear canal and tissue in Rosenthals canal and apical portion of the modiolus was scraped out with a thin knife and needle and tissue placed in incubation medium directly.

Both human and guinea pig SGC were dissected and cut into small pieces and placed in 5 ml 0.25% trypsin. The tubes were placed in 37° C. for 2 min, 3 ml 0.25% trypsin and 0.25 ml DNAase (10 mg/ml) were added. The suspension was gently moved intermittently to obtain optimal loosened cell samples. Three-four min was allowed for sedimentation of larger pieces. Single cell bands were obtained from the supernatant. The process was repeated on remaining large pieces for additional cell samples. Trypsinization was arrested by DMEM+calf serum. Cells were centrifugated for 5 min at 1000 rpm. The cell pellets were then dissolved in medium. Neurobasal+B27+gentamycin and L-glutamin was added. Cells were next incubated on Poly-DL-ornithine coated culture plates. Several nerve growth factors were added in different combinations: BDNF, GDNF, NT-3. In some samples cells were followed day by day and changes observed via inversion light microscopy were photodocumented.

Immunocytochemistry was also performed. The procedure was: following fixation in 4% paraformaldehyde, hSGC were decalcified for 5 weeks in 10% EDTA and buffered at pH 7.4 at 37° C.; embedded in TissueTek and cryosectioned (10 µm-20 µm); labeled with trk antibody sampler kit (Oncogene Research Products catalog #ASK14); secondary labeled via system vectastain ABC kit Elite rabbit PK-6101; and stained with DAB.

Guinea pig nerve cell adhesion to the ornithine layer could be observed at day 3-4. Cell outgrowth could also be seen following adhesion. Under the influence of growth factors added in different combinations, cells showed a growth rate of approximately 100 microns per day. Some neurons demonstrated a fiber length of 1 mm after day 7, indicating a growth of 0.25 microns per day (between day 3 and 7). The cell outgrowth generally started with a polarization of the cell body. Peripheral sprouting occurred frequently at the end of day 10-12. Some cells showed a distal cone-like growth terminal. This terminal showed dense immunostaining against calbindin. Combinations of any of the three neurotrophins studied showed similar outgrowth whereas with a single factor cells demonstrated poor outgrowth. hSGCs were found to express Trk B and Trk C, but not Trk A.

This example demonstrates that it is possible to grow isolated human auditory neurons in vitro, that human SGCs express receptors to neurotrophins, and that they are sensitive to these factors.

Example 5

Effect of 8-Iso-Prostaglandin $F_{2a}$ and Antagonists on Inner Ear Blood Flow

The formation of 8-isoprostane (8-iso-prostaglandin $F_{2a}$) is a marker for free radicals (reactive oxygen species) in the cochlea in response to noise exposure (Ohinata et al., Brain Res. 878, [2000]). This example describes the measurement of the effect of systemic (IV) and local (AICA) F2-isoprostane on CBF, the effect of local (AICA) SQ29548 on F2-isoprostane-induced CBF changes, the effect of intense noise effects on CBF, and the effect of GSH-ME on noise-induced CBF changes.

A local infusion of 8-iso-$PGF_{2a}$ or antagonist SQ29,548 into the cochlear vasculature was made via a glass micropipet inserted into the anterior inferior cerebellar artery (AICA) of the guinea pig. The infusion rate was controlled by a syringe pump. Systemic infusions were achieved via a cannula inserted in the right jugular vein. Changes in cochlear blood flow (CBF) were measured with the fine probe of a laser Doppler flowmeter (LDF) placed on the bony surface of the cochlea. Arterial blood pressure (BP) and heart rate were monitored from a cannula in the right carotid artery. BP and CBF were continuously recorded, as was their ratio (CBF/BP) as a derived measure of cochlear vascular compliance (VC). The results are shown if FIGS. 10-18.

Figure 10:
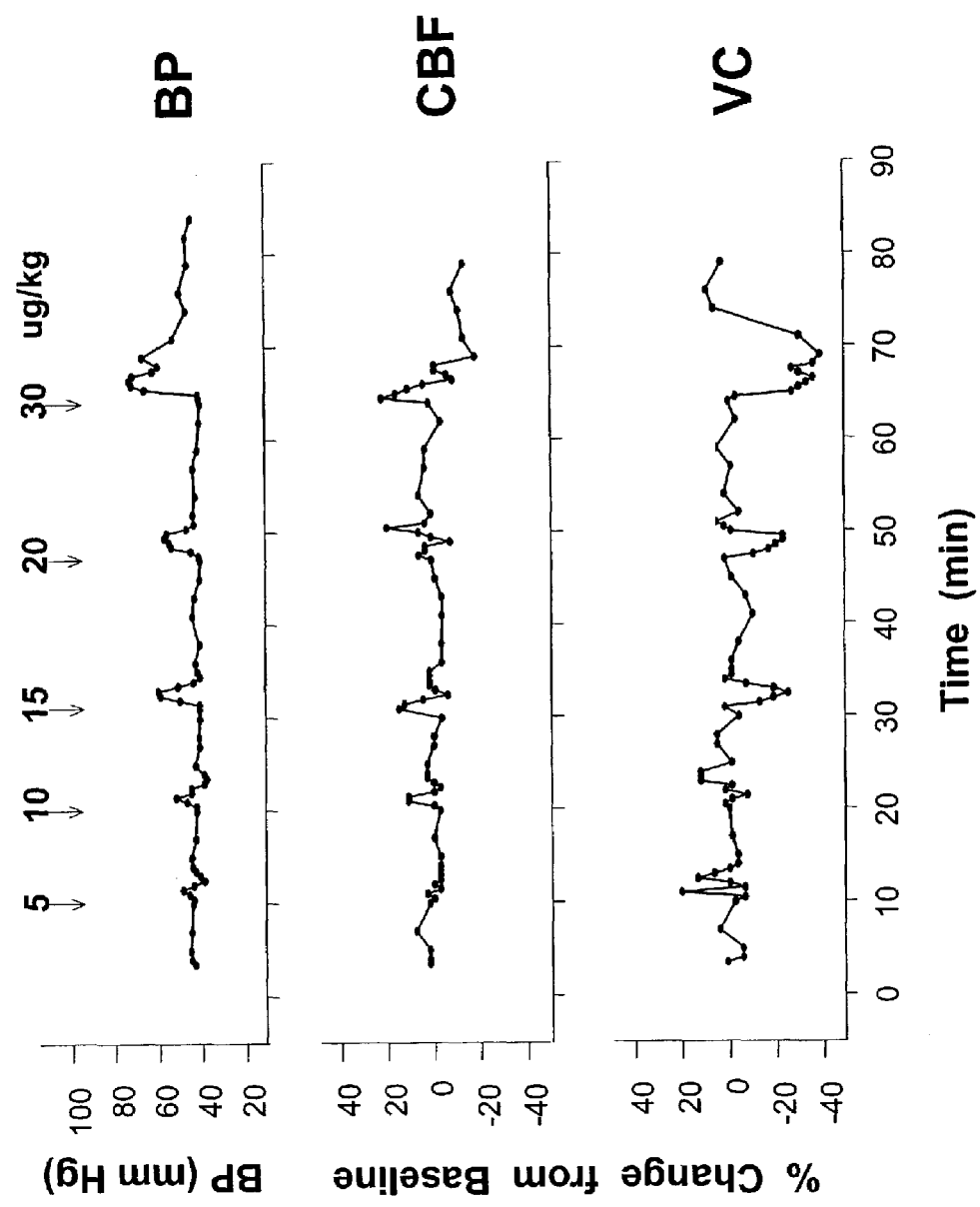
FIG. 10 shows the effects of various i.v. concentrations of 8-iso-$PGF_{2\alpha}$ on VC.

FIG. 10 shows the effects of various i.v. concentrations of 8-iso-$PGF_{2a}$ on VC. 5-30 mg/kg doses of 8-iso-$PGF_{2a}$ were infused intravenously in one guinea pig. Infusion initiation and dosage are indicated by arrows. BP, CBF, and VC all show a dose-related response, with higher doses producing an increasing response in BP and CBF and a related decline in VC response, indicating a dose-dependent constriction of the cochlear vasculature. Baseline is the mean value of the measure 3 min before each infusion.

Figure 11:
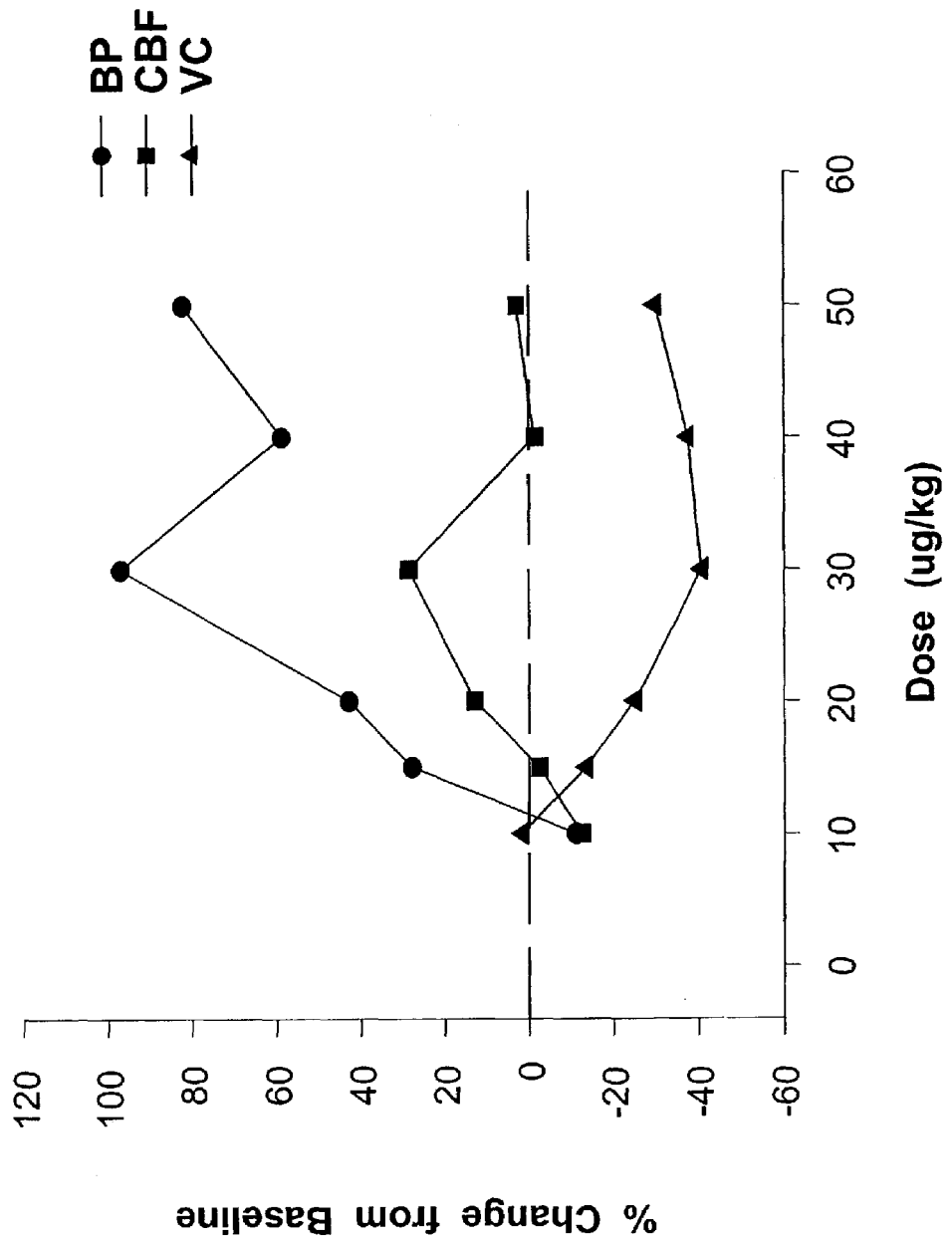
FIG. 11 shows the effect of several i.v. doses of 8-iso-$PGF_{2\alpha}$.

FIG. 11 shows the effect of several i.v. doses of 8-iso-$PGF_{2a}$. Six concentrations (10, 15, 20, 30, 40, 50 mg/kg) of 8-iso-$PGF_{2a}$ were infused intravenously. BP, CBF, and VC responses at 1.5 min after intravenous infusions are shown from one subject. Strong concentration-dependent decrease in VC is evident. The mean value of the 2 min immediately before each dose was used as its baseline.

Figure 12:
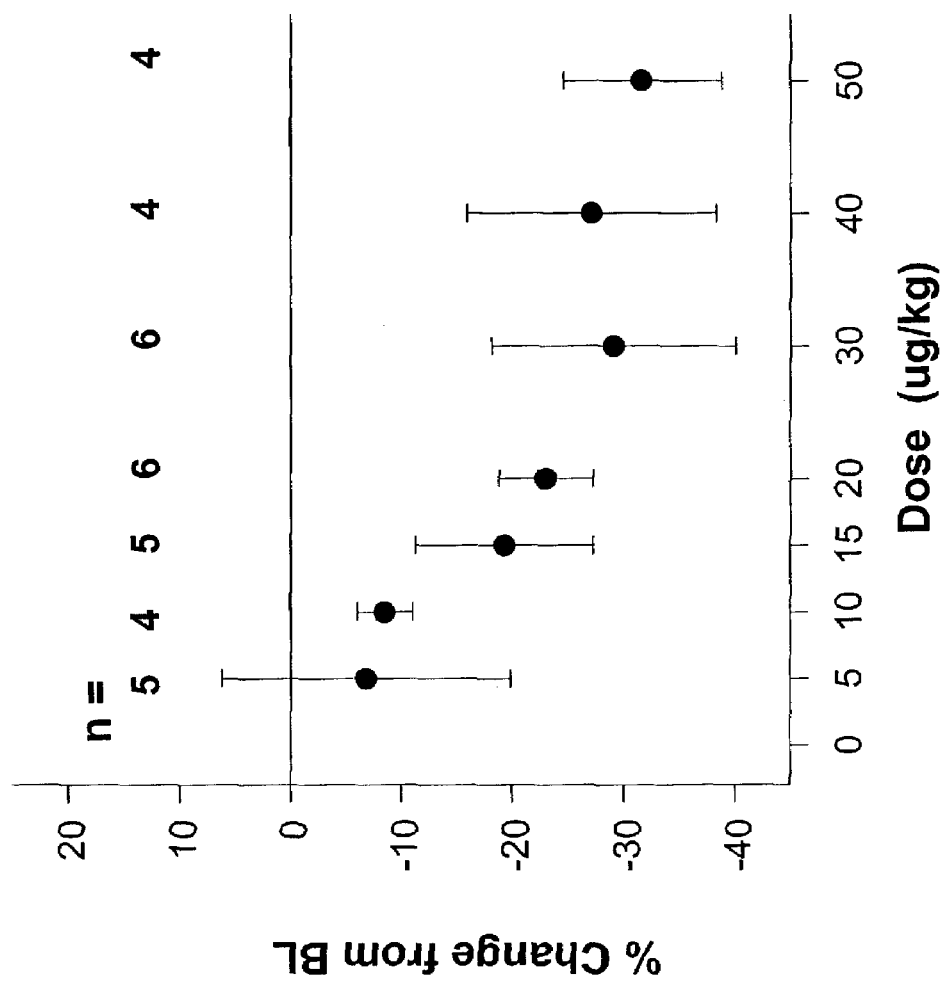
FIG. 12 shows the maximum effect of i.v. 8-iso-$PGF_{2\alpha}$.

FIG. 12 shows the maximum effect of i.v. 8-iso-$PGF_{2a}$. Mean maximum VC response to intravenous 8-iso-$PGF_{2a}$, achieved about 1.5-2.5 min after infusion initiation (mean±SD). There is a clear dose-dependent decrease in VC, which approaches saturation at approximately 30 mg/kg.

Figure 13:
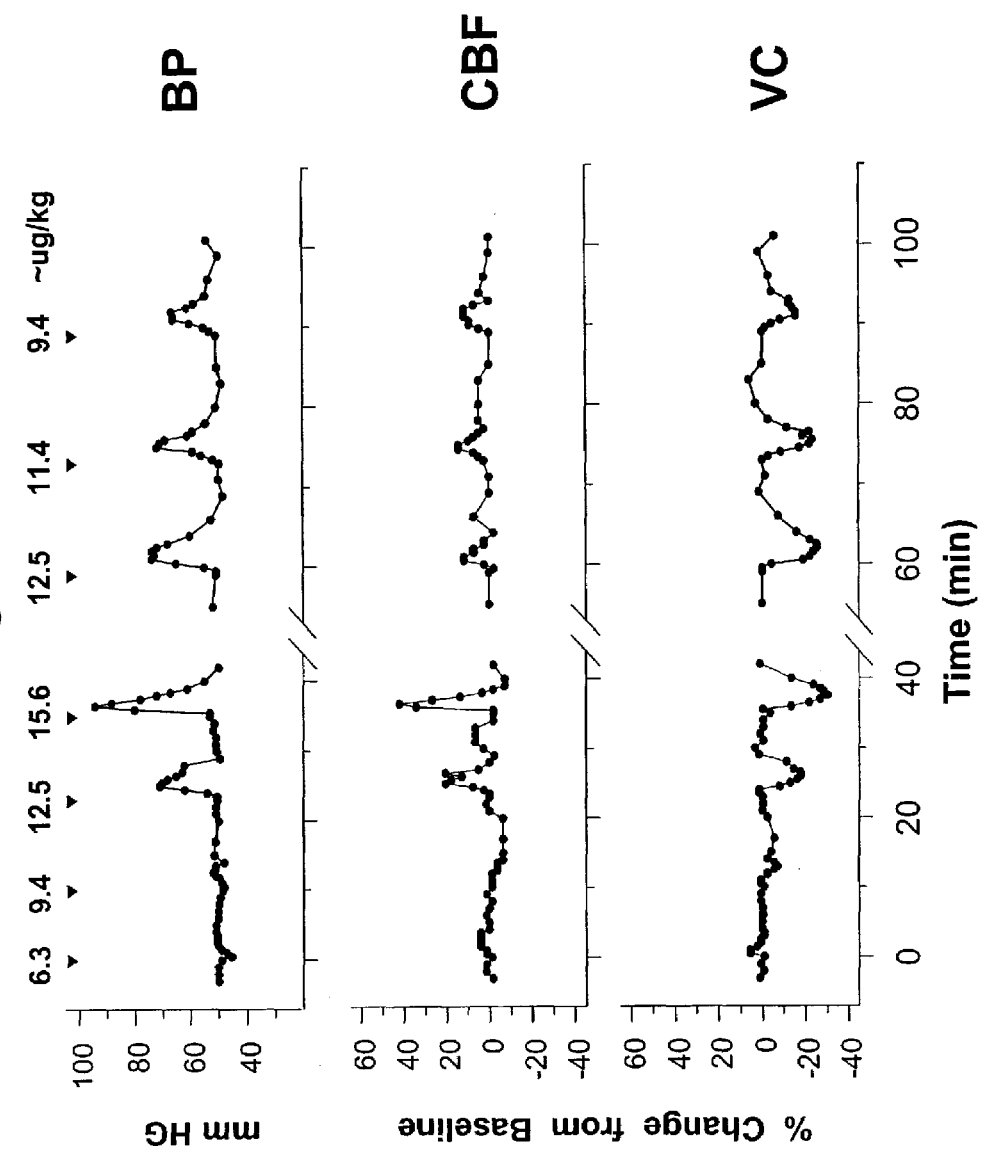
FIG. 13 shows the effects of 8-iso-$PGF_{2\alpha}$ given directly to the inner ear via AICA.

FIG. 13 shows the effects of 8-iso-$PGF_{2a}$ given directly to the inner ear via AICA. Several sequential 1.25 min 8-iso-$PGF_{2a}$ infusions were given via the AICA in one guinea pig. Infusion initiation and dosage are indicated by arrowheads. The dose-related nature of the BP, CBF, and VC responses indicated that there was no significant response to the lower two doses; the next two higher doses show an increasing response in BP and CBF and a related decrease in VC response, indicating a dose-dependent constriction of the cochlear vasculature. The present invention is not limited to a particular mechanism. Indeed, an understanding of the mechanism is not necessary to practice the present invention. Nonetheless, it is contemplated that the modest response to the second 9.4 mg/kg dose may indicate a residual or cumulative level of 8-iso-$PGF_{2a}$ after several doses over an extended time. In addition, in is contemplated that the immediate BP elevation in response to "local" drug delivery reflects a neuronal (cerebellar) mediated cardiovascular effect. Baseline is the mean value of the measure 2-5 min before each infusion.

Figure 14:
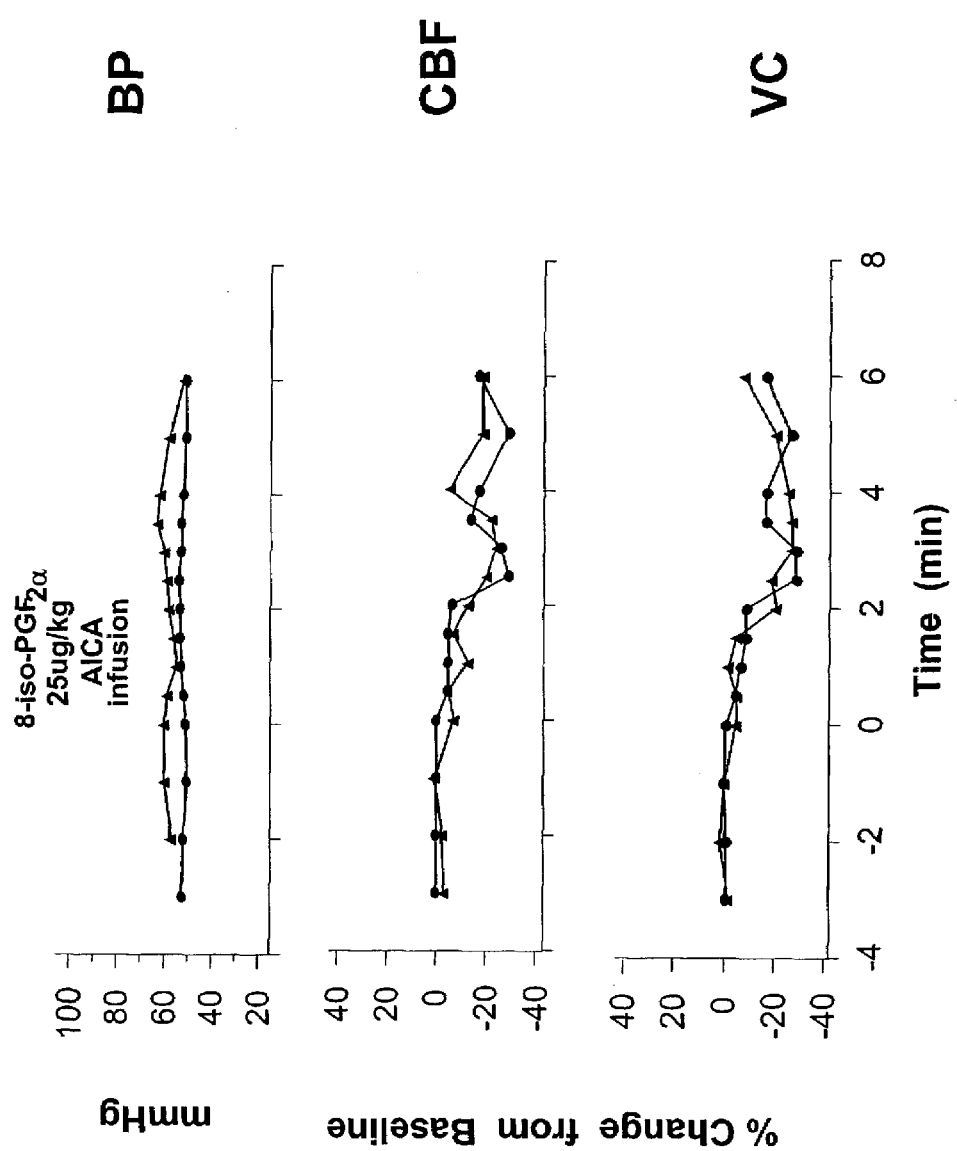
FIG. 14 shows stable BP during AICA infusion of 8-iso-$PGF_{2\alpha}$.

FIG. 14 shows stable BP during AICA infusion of 8-iso-$PGF_{2a}$. In some of the subjects, there was no significant elevation in BP after a 2 min AICA infusion of 8-iso-$PGF_{2a}$, but there was a local vasoconstrictive response (VC) comparable to the VC response associated with the more immediate increase in BP. Two such subjects are shown in FIG. 13.

Figure 15:
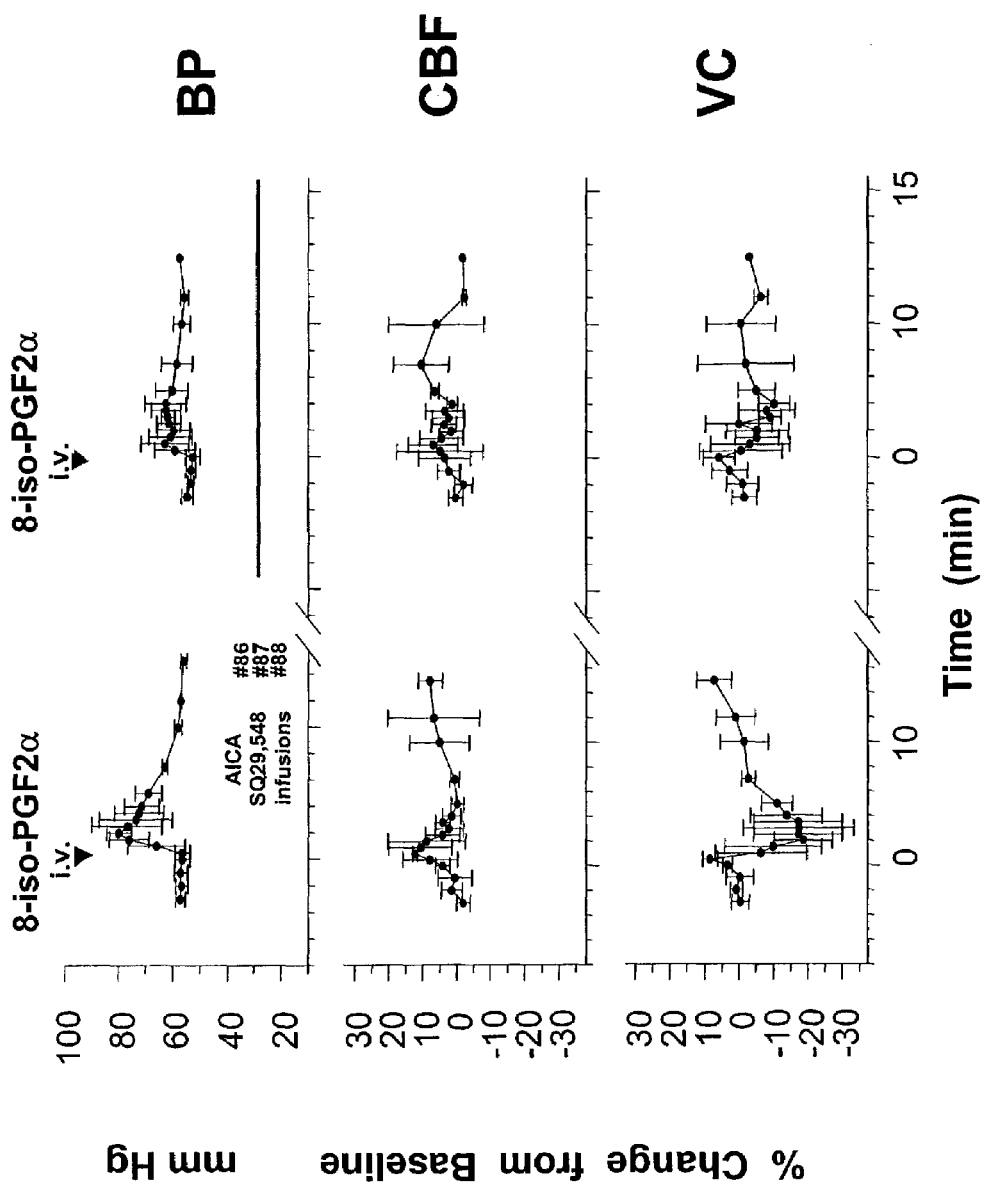
FIG. 15 shows the effect of an 8-iso-$PGF_{2\alpha}$ antagonist on CBF.

FIG. 15 shows the effect of an 8-iso-$PGF_{2a}$ antagonist on CBF. The response of three subjects to 20 sec intravenous infusion of about 75-95 mg/kg 8-iso-$PGF_{2a}$ before and during continuous AICA infusion of its antagonist SQ29,548 (mean±SD) is shown. 8-iso-$PGF_{2a}$ infusions begin at time 0 (arrowheads); each has a 3 min baseline immediately before infusion initiation. SQ29,548 infusion duration for each subject is indicated by the bars in the top panel. The maximum mean VC value during the SQ29,548 infusion was about 8-10% less than after the initial 8-iso-$PGF_{2a}$ infusion, indicating the blocking effect of SQ29,548 on cochlear vascular constriction due to 8-iso-$PGF_{2a}$.

Figure 16:
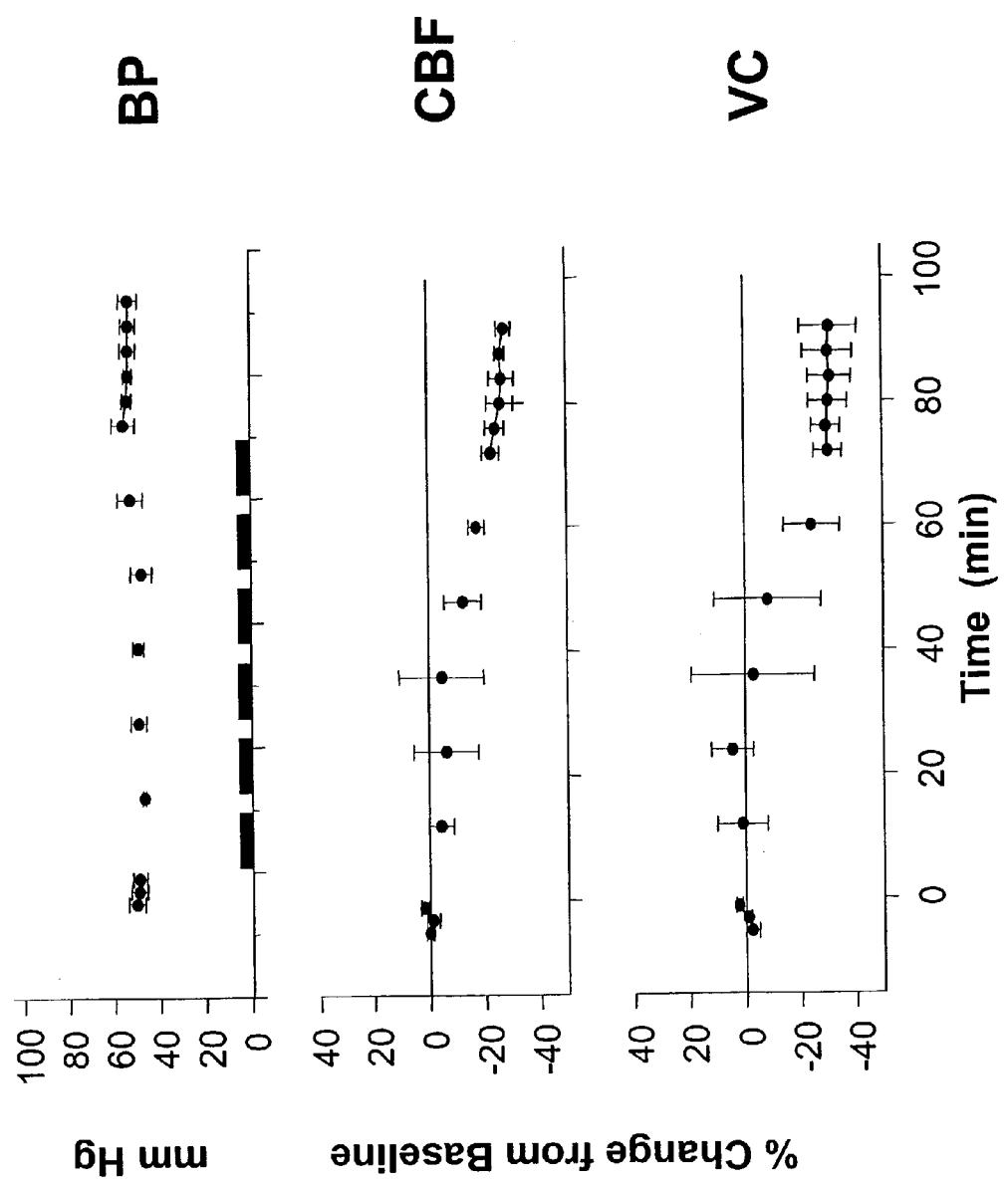
FIG. 16 shows noise-induced vasonstriction.

FIG. 16 shows noise-induced vasonstriction. Three guinea pigs were exposed to high intensity (120 dB) noise for one hour (6×10 min, red lines in top panel). BP, CBF, and VC measurements were made during 2-min off-noise periods. Over the course of the exposure, there was pronounced vasoconstriction (VC) and decrease in cochlear blood flow (CBF), while BP remained stable (mean±SD).

Figure 17:
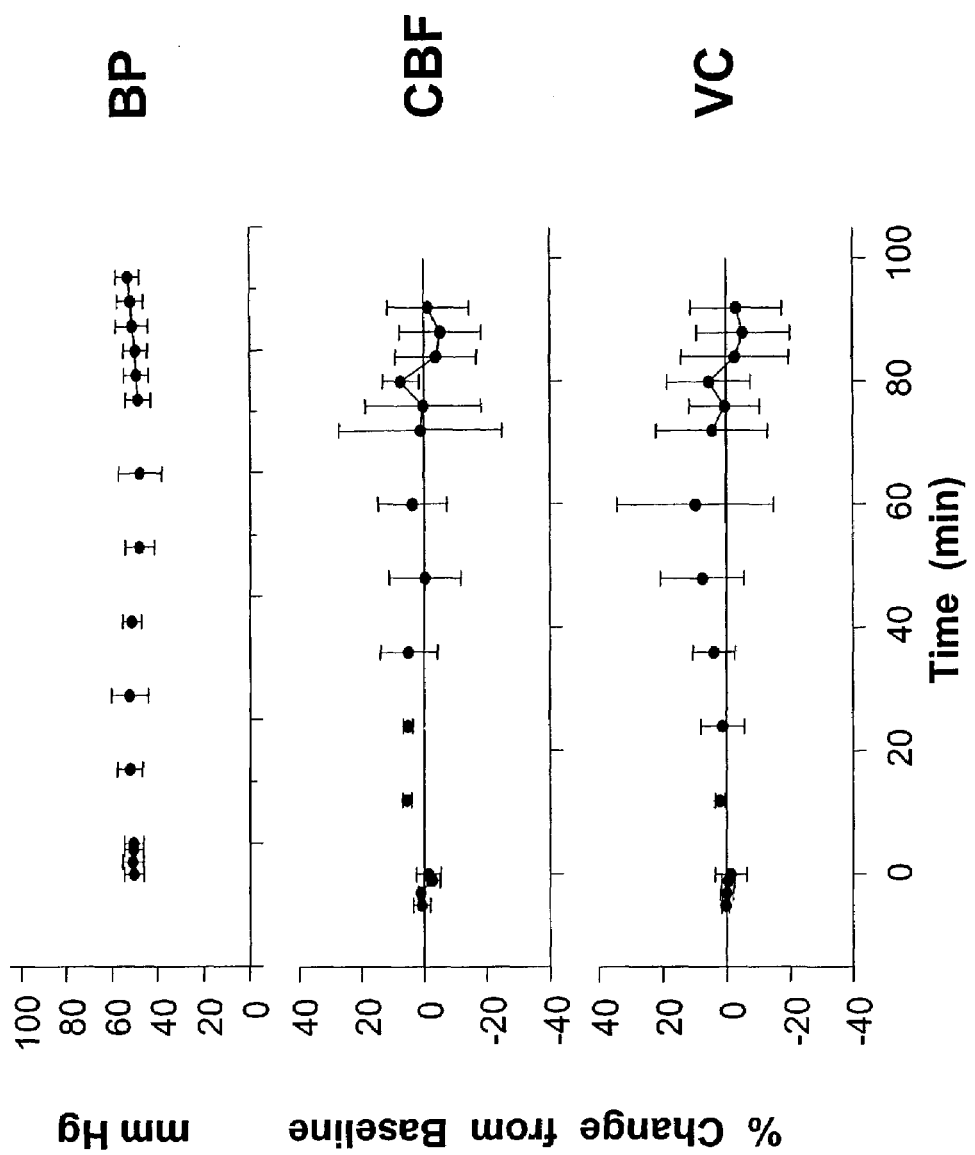
FIG. 17 shows the effect of GSHE on noise-induced vasoconstriction.

FIG. 17 shows the effect of GSHE on noise-induced vasoconstriction. Noise exposure was as in FIG. 15. However, when the antioxidant glutathione-monoethyl ester (GSHE) was given intraperitoneally 1 hour before noise exposure, the effect of noise on CBF and VC was eliminated.

Figure 18:
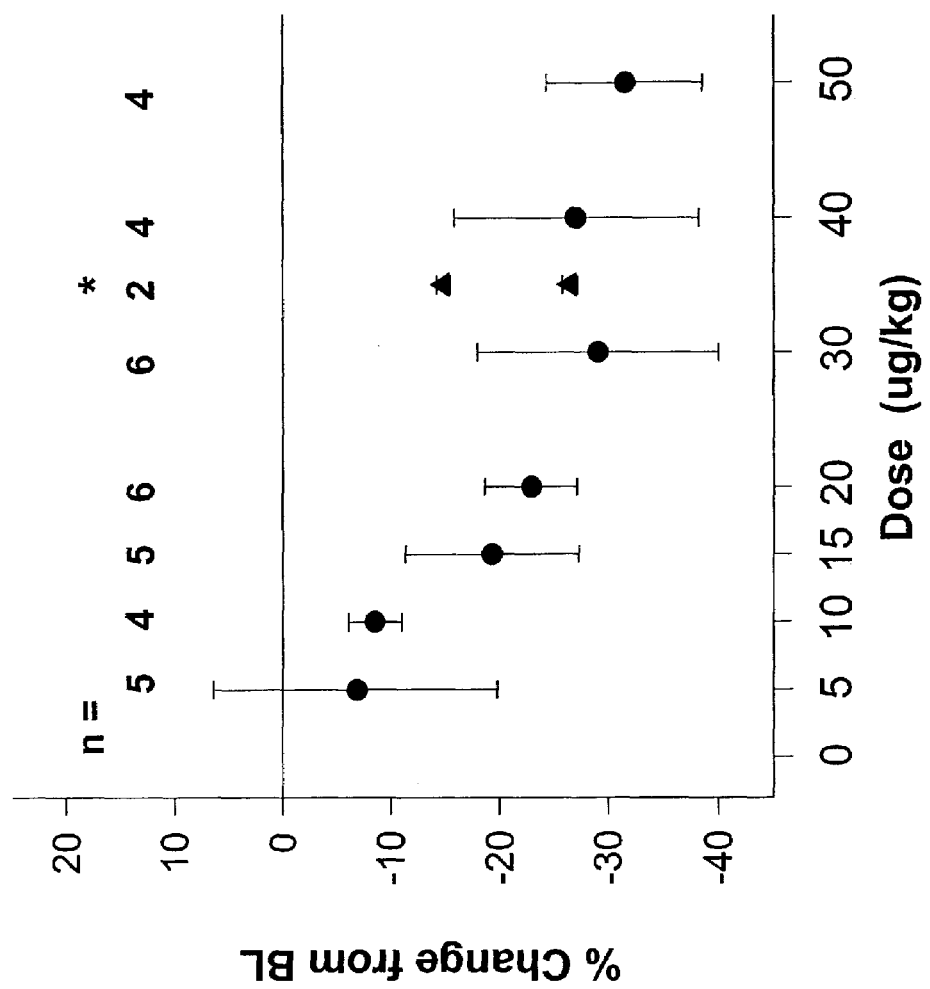
FIG. 18 shows the maximum effect of 8-iso-$PGF_{2\alpha}$ on VC.

FIG. 18 shows the maximum effect of 8-iso-$PGF_{2a}$ on VC. Mean maximum response of two subjects to 35 mg/kg 8-iso-$PGF_{2a}$ i.v. before (lower triangle) and after (upper triangle) AICA infusion of antagonist SQ29,548. There was 12% decrease in cochlear vascular constriction.

The results indicated that there was rapid and concentration-dependent change in blood pressure (BP) and CBF following administration of 8-iso$PGF_{2a}$, followed by recovery toward baseline. The ratio of CBF to BP, as a specific measure of cochlear vascular conductance (VC), showed a strong dose-dependent decrease, indicating a constriction of the cochlear vasculature, reducing CBF. AICA infusion of ~25 μg/kg 8-iso$PGF_{2a}$ over 2 min and minimal BP change resulted in a rapid 25-30% decrease in CBF and VC. The addition of the antagonist SQ29,548 blocked VC by iso$PGF_{2a}$.

Example 6

Enhanced Recovery from Noise Over Stimulation Correlates with HSP Expression

Noise over stimulation at levels that induce temporary threshold shift (TTS) has been shown to transiently induce heat shock proteins (HSPs) HSP 72 and HSP 27 in rat cochlear outer hairs cells (Lim et al., Hear Res., 69:146 [1993]; Altschuler et al., 1996). TTS noise exposure also improves recovery from a second noise exposure, four hours later, that would normally be damaging (a PTS or permanent threshold shift exposure). In this Example, a group was added where the second PTS exposure was 18 hours after the first TTS exposure, when there is no longer HSP expression from the first TTS exposure. The results demonstrated that protection correlates with HSP expression.

A. Methods

Experimental Design

Animals were randomly divided into three groups of six animals each: Control, Protection, and Post-protection (see FIG. 19). For all animals, baseline ABR threshold level was assessed to ensure normal hearing. Control animals were only exposed to a PTS noise stimulation (109 dB OBN centered on 12 kHz, for 90 minutes at a 100% duty cycle). ABRs were collected immediately after and 4 hours after cessation of noise. Protection and Post-protection animals were exposed to a TTS noise stimulus (110 dB broad band noise for 90 minutes at a 50% duty cycle) prior to a PTS exposure identical to that used for Control subjects. Animals in the Protection and Post-protection groups differed in the delay between TTS and PTS exposures. Subjects in the Protection group had ~4 hour delay between the termination of TTS exposure and initiation of PTS exposure; the exact timing varied somewhat, as ABR assessment was initiated at 4 hours post-TTS, and PTS exposure was initiated immediately upon completion of the ABR. In contrast, animals in the Post-Protection group had an 18 hour delay between TTS exposure termination and PTS exposure initiation.

In all cases, animals were anesthetized (xylazine (8 mg/kg, IM) and ketamine (75 mg/kg, IM)) for both ABR assessment and noise exposure. Level of anesthesia was assessed by monitoring respiration, as well as by response to toe pinch, with supplemental doses of anesthetic provided as needed to maintain a relatively constant state of anesthesia. Body temperature was maintained using isothermal heating pads during ABR assessment and noise exposure, and by overhead heat lamps while animals were in micro-isolator cages awaiting/following noise exposure. Because anesthetic level and body temperature were maintained throughout the experiment, anesthetic controls were not included in the study.

Subjects

Sprague Dawley rats (Charles River Laboratories, Willmington, Mass.) weighing between 250-500 gms were used in this investigation. Prior to inclusion in the study, animals were assessed for normal hearing, as demonstrated by auditory brainstem response (ABR) threshold level (<30 dB SPL required for inclusion in the study). All experimental protocols and procedures were reviewed and approved as consistent with NIH guidelines for the humane treatment of experimental animals by the University of Michigan Committee on the Use and Care of Animals.

Acoustic Auditory Brainstem Responses

Acoustic auditory brainstem response (ABR) measures were obtained prior to noise exposure (baseline), immediately (within 10 minutes of noise termination) after each noise exposure, and 4 hours after each noise exposure. In all cases, animals were anesthetized (xylazine (8 mg/kg, IM) and ketamine (75 mg/kg, IM)) during ABR assessment. Body temperature was maintained by use of an isothermal heating pad located directly under each subject.

Responses were recorded with subdermal recording needle electrodes placed at vertex (active) against a reference placed at the midline of the skull approximately 2 cm anterior to bregma. A subcutaneous electrode in the thigh served as the ground. In a soundproof room, computer generated alternating polarity pulses (160 µs, 50 pps) of octave-band-noise (OBN) centered on 18 kHz were delivered to a transducer positioned at the auditory meatus (contacting the canal), directed along the axis of the canal. Responses were amplified by a Grass P15 amplifier (gain=100), with a filter bandpass of 30 Hz to 3 kHz; in-house software was used to display the 10 second stimulus-locked average. Stimuli were calibrated with a Bruel and Kjaer ½" condenser microphone. A mean of 1024 samples of electrophysiological activity was recorded for stimuli close to threshold. Stimuli were provided at intensities in 5 dB intervals to a maximum level of 102 dB SPL. Threshold was defined as the lowest stimulus intensity that evoked at least a 0.2 µV (peak to peak, with a latency between 1.6 and 3.2 ms) replicable waveform.

Noise Exposures

Two noise exposure paradigms were utilized: a TTS exposure and a PTS exposure. The TTS noise consisted of broad band noise (BBN) at an intensity of 110 dB SPL, on a 50% duty cycle (on for 500 ms, off for 500 ms, for each second of the total stimulus duration) for 90 minutes. This is identical to the exposure paradigm used previously to induce expression of hsp 70 in the rat cochlea (Lim et al., Hear Res., 69:146 [1993]). PTS noise consisted of octave-band-noise (OBN) centered at 12 kHz, at an intensity of 109 dB SPL for 90 minutes.

Noise exposures were carried out in a lighted, ventilated sound-attenuating chamber. Animals were exposed two at a time, in separate cages. Cages were placed on a turntable (1 rpm) for the duration of sound exposure. All noise was produced by a random noise generator (General Radio Company), attenuated (resistor network), band-pass filtered (Rane), amplified (Parasound) and delivered to a horn speaker (JBL) mounted directly overhead, oriented straight down over the turn-table. Filter bands for the two exposure paradigms were as follows: 630 Hz-20 kHz for TTS noise, and 10-20 kHz for PTS noise. TTS noise was gated at a 50% duty cycle prior to amplification. Intensities were set to appropriate levels using a Bruel and Kjaer ½" condenser microphone and a modular precision sound level meter (Type 2231) at the center of the sound chamber where the animals were placed, as well as at multiple positions throughout the room to ensure stimulus uniformity.

Data Analysis

For animals whose thresholds were greater than 102 dB SPL, the maximum limits of ABR recording on our system, a value of 102 dB was used in plotting data and for calculation of threshold shifts for comparison to other animals and groups. Accordingly, threshold shifts for these animals are underestimates of the actual threshold shift. Statistical evaluation of significance was performed by repeated measures analysis of variance (2-way RM ANOVA) followed by a Student-Newman-Keuls all pairwise comparison test. A criterion of p=0.05 was used to determine statistical significance.

B. Results

Figure 19:
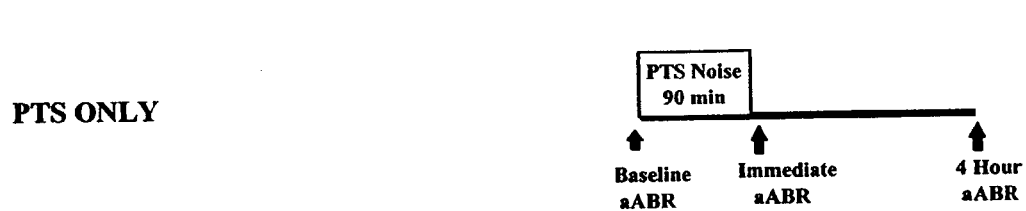
FIG. 19 shows a schematic of experimental design and timing of noise exposures for each of the three groups.
Figure 20:
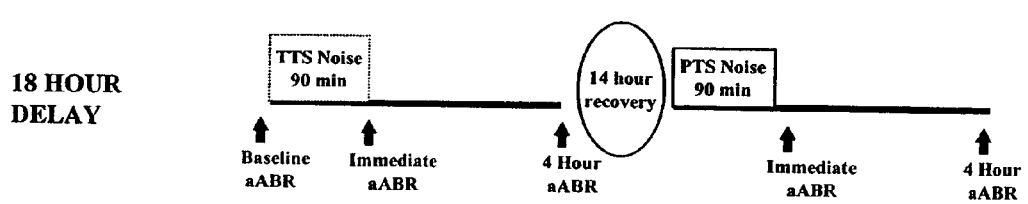
FIG. 20 shows aABR thresholds for all animals, by group.
Figure 21:
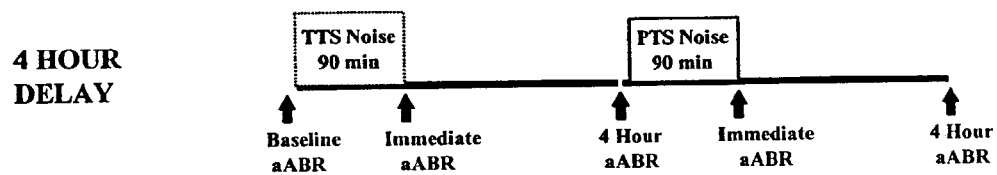
FIG. 21 shows mean and standard deviations of aABR threshold shifts for each group immediately and 4 hours following TTS and/or PTS noise.

Results are shown in FIGS. 19-21. FIG. 19 shows a schematic of experimental design and timing of noise exposures for each of the three groups. FIG. 20 shows aABR thresholds for all animals, by group. (A) ABR thresholds for animals in the PTS group. (B) ABR thresholds for all animals in the Post-Protection (18 hour delay) group. Animals in this group had thresholds that were greater than the maximum level of the ABR recording system, such that the calculated threshold shifts underestimate the true threshold change. (C) ABR threshold for all animals in the Protection (4 hour delay) group. Three of the six animals (2xn10, 2xn14, and 2xn15) demonstrated a complete recovery from the PTS noise within 4 hours. FIG. 21 shows mean and standard deviations of aABR threshold shifts for each group immediately and 4 hours following TTS and/or PTS noise. There was no statistically significant difference threshold shift immediately or four hours after TTS exposure. There was, however, a statistically significant difference between all groups 4 hours following PTS noise (ANOVA, Student Newman-Keuls test p<0.05).

Threshold shifts immediately following TTS exposure were on the order of 10-60 dB with a maximum residual loss of 10 dB at 4 hours post-exposures. While the degree of TTS was variable across subjects, and there was a trend of greater threshold shifts in the Post-Protection group (average shift of 31+/−19 dB) group than in the Protection group (average shift 19+/−20 dB) group, the difference was not statistically significant (2-way RM ANOVA, p=0.21). There was a statistically significant improvement in threshold 4 hours post-TTS, relative to the threshold obtained immediately post-TTS (p=0.002); treatment group had no significant interaction with this threshold change (p=0.48).

Following PTS exposure, the treatment groups differed not only in the magnitude of the initial threshold shift, but also in the degree of recovery of threshold shift over the 4-hour recovery period. For control animals, PTS exposure resulted in an average threshold shift of 56±28 dB (mean±s.d.) immediately following cessation of noise stimulation, with minimal improvement four hours post-exposure (47±34 dB). Half of the subjects in this group had stable thresholds over the recovery period (i.e., no recovery), while the other subjects showed partial improvement, and in one case, complete recovery. For Protection animals, threshold shifts averaged 43±31 dB immediately post-exposure and 12±14 at 4 hours following PTS noise exposure. Three subjects in this group (2xn10, 2xn14, and 2xn15) demonstrated a complete recovery of threshold level by 4 hours post-PTS exposure; the remaining subjects in the group had substantial, albeit incomplete, recovery of threshold sensitivity relative to baseline after the 4-hour recovery period. For Post-Protection subjects, in contrast, threshold shifts were stable over the 4-hour recovery period for all subjects, averaging 83±6 dB at both time points assessed.

Comparison across groups (2-way RM ANOVA) demonstrated statistically significant differences between treatment groups (p=0.002), which were dependent on the time-point of interest (immediately post-PTS vs. 4 hrs post-PTS; p=0.005). Multiple pairwise comparison (Student-Newman-Keuls method) demonstrated statistically significant differences in threshold shift between all three groups at 4 hours post-PTS exposure; no other significant differences were identified.

Example 7

Noise-Induced Lipid Peroxidation in the Cochlea

This example describes the influence of the N-methyl-D-aspartate (NMDA) receptor antagonist ((+)-MK-801), its isomer ((−)-MK-801), the nitric oxide synthase (NOS) inhibitor L-N$^{\omega}$-Nitroarginine methyl ester (L-NAME), the anti-oxidant N-acetylcysteine (NAC), and the selective NR1/2B NMDA receptor antagonist PD 174494 on noise-induced permanent threshold shift, hair cell loss, and lipid peroxidation in the cochlea.

A. Methods

Animals

Pigmented guinea pigs (250 to 300 g; Elm Hill Breeding Laboratory, Chelmsford, Mass.) with normal Preyer's reflex were used in this study. Only male animals were used. The animals were on a normal day/night cycle. The experimental protocol was approved by the Animal Care and Use Committee at the University of Michigan and conforms to the National Institutes of Health Guidelines for the Care and Use of Laboratory Animals.

Experimental Schedule

Each animal received a drug dose before either being noise-exposed for 5 hours or simply placed in the exposure chamber for 5 hours. Auditory brain stem responses (ABR) were measured 2 days before and 10 days after noise exposure or sham exposure. Immediately after the second ABR measurement, animals were sacrificed for histological examination or for measurement of 8-isoprostane.

Drug Administration

Animals were assigned to one of 17 groups (see Table 3). Eight groups were used to assess the effects of these agents on noise-induced threshold (auditory brain stem response, ABR) sensitivity and hair cell damage (cytocochleogram). Nine groups were used to determine the effects on noise-induced lipid peroxidation. Groups were injected intraperitoneally with 5 ml/kg of 0.9% NaCl, 0.2 mg/ml (+)-MK-801, 0.2 mg/ml (−)-MK-801, 0.2 mg/ml L-NAME, 100 mg/ml NAC, or a mixture of 0.2 mg/ml (+)-MK-801 and 100 mg/ml NAC 30 min before being placed in the exposure chamber. Because of the high clearance of PD 174494, one group of animals received 5 ml/kg of 2 mg/ml PD 174494 intraperitoneally 30 min before and 2 hr into noise exposure. A control group received 5 ml/kg of 0.9% NaCl on the same time schedule.

(+)-MK-801, (−)-MK-801, and L-NAME were dissolved in 0.9% NaCl to make a concentration of 0.2 mg/ml. NAC was dissolved in distilled water and pH was adjusted to 7.5 with 1 M NaOH, with a final concentration of 100 mg/ml. PD 174494 was dissolved in 1 M HCl and pH was adjusted to 6.0-6.5 with 1 M NaOH.

Auditory Brainstem Responses

Animals were anesthetized with xylazine (10 mg/kg) and ketamine (40 mg/kg) given intramuscularly. A differential active needle electrode was placed subcutaneously below the test ear and a reference electrode at the vertex. A ground electrode was positioned below the contralateral ear. The sound stimuli consisted of 15 ms tone bursts, with a rise-fall time of 1 ms at frequencies of 2, 4, 8, 16 and 20 kHz, and were generated using a Fordham Audio Generator (Model AG-298, Fordham Radio Supply, Hauppauge N.Y.). They were presented to the right external auditory meatus in a closed acoustic system through an ear bar connected to a transducer (Beyer DT-48, Beyer Dynamic, Farmingdale N.Y.). The sound intensity was varied by 5 dB intervals. One thousand twenty-four tone presentations given at the rate of 9 s$^{-1}$ were averaged using a microcomputer and custom software to obtain a waveform. Hearing threshold was defined by the consistent appearance of ABR peaks III or IV. Test/retest reliability was within 5 dB. After the second ABR measurement, the cochleae were harvested.

TABLE 3

| Group Drug | Time of Administration | Volume | N | ABR Noise |
|---|---|---|---|---|
| Combined | | | | |
| 1 NaCl | * | 5 ml/kg | 8 | + |
| 2 +-MK-801 | * | 5 ml/kg | 8 | + |

TABLE 3-continued

ABR

| Group | Drug | Time of Administration | Volume | N | Noise |
|---|---|---|---|---|---|
| 3 | (−)-MK-801 | * | 5 ml/kg | 7 | + |
| 4 | L-NAME | * | 5 ml/kg | 7 | + |
| 5 | NAC | * | 5 ml/kg | 7 | + |
| 6 | (+)-MK-801 + NAC | * | 5 ml/kg | 6 | + |
| 7 | NACL | *, # | 5 ml/kg × 2 | 8 | + |
| 8 | PD174494 | *, # | 5 ml/kg × 2 | 9 | + |

TABLE 4

8-Isoprostane

| Group | Drug | Time of Administration | Volume | N | Noise |
|---|---|---|---|---|---|
| Combined | | | | | |
| 9 | NaCl | * | 5 ml/kg | 5 | − |
| 10 | NaCl | * | 5 ml/kg | 6 | + |
| 11 | (+)-MK-801 | * | 5 ml/kg | 6 | + |
| 12 | (−)-MK-801 | * | 5 ml/kg | 7 | + |
| 13 | L-NAME | * | 5 ml/kg | 5 | + |
| 14 | NAC | * | 5 ml/kg | 5 | + |
| 15 | (+)-MK-801 + NAC | * | 5 ml/kg | 4 | + |
| 16 | NaCl | *, # | 5 ml/kg × 2 | 6 | + |
| 17 | PD174494 | *, # | 5 ml/kg × 2 | 6 | + |

*: 30 mm before noise
: 2 hours after noise

Noise Exposure

Animals were exposed to noise in a lighted and ventilated sound exposure chamber while having free access to food and water. The sound chamber was fitted with speakers driven by a noise generator and a power amplifier. Using a ½-inch Bruel and Kjaer condenser microphone and Fast Fourier Transform analyzer, sound levels were measured and calibrated at multiple locations within the sound chamber to ensure uniformity of the stimulus. The stimulus intensity varied by a maximum of 3 dB across measured sites within the exposure chamber. Animals were individually subjected to 4 kHz octave band noise, 115 dB SPL for 5 hours. Two hours after initiation, noise exposure was interrupted for 10 min to perform the second injection of 0.9% NaCl or PD 174494 in groups requiring it.

Hair Cell Count

Animals were sacrificed under deep anesthesia. The bullae were quickly removed and transferred into 4% paraformaldehyde in 0.01 M phosphate-buffered saline (PBS)(pH 7.4). The bone near the apex, round window, and oval window was opened, followed by two gentle local perfusions from the apex with 1 ml of 4% paraformaldehyde each. The tissue was kept in the fixative for 12 hr. After removal of the bony capsule and the lateral wall tissues, the modiolar core including the organ of Corti was removed from the temporal bone. Following permeabilization with 0.3% Triton X-100 for 10 min, whole-mounts of the organ of Corti were stained for actin with fluorescent phalloidin for 30 min to outline hair cells and their stereocilia for a quantitative assessment (Raphael and Altschuler, Hear. Res., 31:173 [1991]). Slide preparations were observed under fluorescence microscopy and missing (as shown by scar formation) and present (as shown by intact stereocilia) hair cells in the sensory epithelium were counted from the apex to the base in 0.19 mm segments. Percent hair cell loss was calculated for each segment. A group mean cytocochleogram was created by averaging the loss at each segment. Differences were evaluated for statistical significance on the basis of data from the region 9-13 mm from apex, the region of greatest damage in a previous study (Ohinata et al., Hear. Res. 146: 28 [2000]).

Measurement of 8-Isoprostane

Animals were anesthetized with xylazine (10 mg/kg) and ketamine (40 mg/kg) given intramuscularly and decapitated. The auditory bullae were removed and the bony capsule of the cochlea was immediately opened.

Guinea pig cochleae were dissected in ice-cold Hanks' balanced salt solution (HBSS, Gibco Laboratories, Grand Island, N.Y.: 1.25 mM $CaCl_2$, 5.55 mM glucose, 0.81 mM $MgSO_4$, 0.44 mM $KH_2PO_4$, 136.9 mM NaCl, 0.34 mM $Na_2HPO_4$, 5.4 mM KCl, 5.0 mM sodium HEPES, with pH titrated to 7.4 (with NaOH) and osmolality adjusted to 300±1 mOsm with NaCl). Lateral wall tissues (spiral ligament and stria vascularis) and organ of Corti were removed from the modiolar core. The tissues were transferred to a 0.05% dl-dithiothreitol solution to prevent auto-oxidation of arachidonic acid and homogenized with a homogenizer for 30 sec. The homogenate was centrifuged at 7,200×g for 15 min at 4° C. Proteins were measured in aliquots of the supernatant by the Bradford method (Bradford, Anal. Biochem. 72: 248 [1976]). Butyl hydroxytoluene was added to the supernatant to a concentration of 0.1%, followed by 200 µl of ethanol and another homogenization. The homogenate was centrifuged at 1,500×g for 10 min at 4° C. Two hundred µl of 15% KOH was added to the supernatant for determination of the levels of free and esterified 8-isoprostane, and the mixture was incubated at 40° C. for 1 hr. The solution was then acidified to pH 3 with HCl. The samples were applied to octadecylsilyl silica columns pre-activated with methanol and distilled water and subsequently washed with distilled water and then with hexane. 8-isoprostane was eluted with ethyl acetate containing 1% methanol, and the eluate was evaporated under $N_2$ to dryness. The samples were dissolved in 30 µl of acetone and spotted on silica gel G thin layer chromatography plates, which were developed in chloroform/methanol/acetic acid/water (80:18:1:0.8, v/v). 8-isoprostane was located from the $R_f$ of standards run on the same plate and visualized by spraying with 3.5% phosphomolybdic acid. The bands corresponding to 8-isoprostane were scraped off the plate and transferred to a centrifuge tube. 8-isoprostane was eluted by adding 1.5 ml of ethanol and the supernatant was dried under $N_2$ after centrifugation.

8-isoprostane was measured by enzyme immunoassay based on the competition between 8-isoprostane and an 8-isoprostane-acetylcholinesterase conjugate for a limiting amount of 8-isoprostane polyclonal antiserum (Cayman Chemical, Ann Arbor, Mich.). Dried samples containing extracted 8-isoprostane were reconstituted in 1 ml of 100 mM phosphate buffer (pH 7.4) with 1.5 mM $NaN_3$, 0.4 M NaCl, 1 M EDTA, and 1 mg/ml BSA. Fifty-µl samples were placed in microtiter wells precoated with mouse monoclonal anti-rabbit IgG. 50 µl of acetylcholinesterase linked to 8-isoprostane (tracer) were added, and the samples were incubated for 18 hr at room temperature. Unbound reagents were removed by washing five times with 10 mM phosphate buffer (pH 7.4) containing 0.05% Tween 20, and the plates were developed for 90 min with the acetylcholinesterase substrate acetylthiocholine as well as 5,5'-dithio-bis-[2-nitrobenzoic acid] (DTNB; Ellman's reagent). Plates were read on a Microplate EL311 (BIO-TEK Instruments INC., Winooski, Vt.) at 415 nm. Calibration curves were prepared from standard samples at a concentration range of 4 to 500 pg/ml.

Chemical Reagents

HBSS was from Gibco Laboratories (Grand Island, N.Y.). 8-isoprostane-acetylcholine-acetylcholinesterase, 8-isoprostane polyclonal antiserum and 8-isoprostane were from Cayman Chemical (Ann Arbor, Mich.). All other reagents were obtained from Sigma Chemical Co. (St. Louis, Mo.). PD 174494 was provided by Dr. Peter A. Boxer (Department of Chemistry, Parke-Davis Pharmaceutical Research, division of Warner-Lambert Company, Ann Arbor, Mich.).

Data Analysis

All values are presented as means±sd. Differences between mean values were evaluated using one-way ANOVA followed by Student-Newman-Keul's as a post hoc test. A p value of <0.05 was considered significant.

B Results

Threshold Shifts Following Noise Exposure

There was no significant difference in the threshold levels before noise exposure among groups. Permanent threshold shifts were assessed 10 days after noise exposure, since preliminary experiments showed thresholds were stable by this time. The average threshold shifts 10 days after noise exposure in the group receiving 0.9% NaCl were 29±11 dB SPL (at 2 kHz), 48±10 dB SPL (at 4 kHz), 40±13 dB SPL (at 8 kHz), 29±15 dB SPL (at 16 kHz), and 19±15 dB SPL (at 20 kHz). As a control for the PD 174494 group, eight animals were injected with 0.9% NaCl twice. Because there was no difference in threshold shifts between single and double injected animals, these groups were combined and analyzed as one control group. Pretreatment with (+)-MK-801 significantly attenuated threshold shifts at all frequencies. In the (−)-MK-801 group, the threshold shift decreased significantly only at 2 kHz; there was no effect at other frequencies. With L-NAME, threshold shift was significantly attenuated at 2 kHz but, conversely, was increased at 20 kHz. NAC significantly attenuated threshold shifts at all frequencies. The treatment of (+)-MK-801 plus NAC attenuated threshold shifts at all frequencies and showed, compared to the effects with individual administrations, further partial protection; however, the difference was not statistically significant. PD 174494 significantly attenuated noise-induced hearing loss at 2, 4 and 8 kHz.

Hair Cell Count

For the ears in the (+)-MK-801 and the 0.9% NaCl groups, quantitative assessment of organ of Corti whole-mounts showed that peak damage to the outer and inner hair cells was in the region 9 to 13 mm from the apex. Peak damage in cytocochleograms for other groups also was in the same region. Since there was no difference in hair cell loss between the two 0.9% NaCl groups, they were combined and analyzed as one control group. (+)-MK-801, NAC, and their combined treatment attenuated outer and inner hair cell loss. PD 174494 protected only inner hair cells. In the L-NAME treatment group, mean inner hair cell loss increased, while outer hair cell loss was not affected.

Measurement of Cochlear 8-Isoprostane

Because there was no difference in 8-isoprostane levels in the organ of Corti, lateral wall, and modiolar core between the single and double 0.9% NaCl injection groups, they were combined and analyzed as one control group. The levels of 8-isoprostane increased 6-fold in the organ of Corti, 5-fold in the lateral wall tissue, and 9-fold in the modiolar core immediately after noise exposure. (+)-MK-801 attenuated the 8-isoprostane increase in the organ of Corti and the modiolar core but not in the lateral wall. Compared with 0.9% NaCl, (−)-MK-801 did not affect the 8-isoprostane level in the cochlea after noise exposure. L-NAME suppressed 8-isoprostane formation during noise exposure in the lateral wall and modiolar core. NAC and the combined (+)-MK-801/NAC treatment attenuated 8-isoprostane increase in the organ of Corti, lateral wall, and modiolar core. PD 174494 administration suppressed 8-isoprostane elevation of in the organ of Corti and modiolar core. The effect of PD 174494 on 8-isoprostane formation in these regions was about half that of (+)-MK-801.

Correlation of Threshold Shift, Hair Cell Loss, and Cochlear Level of 8-Isoprostane There was significant correlation between threshold shift at 4 kHz and hair cell loss at 9-13 mm, where maximum hair cell loss was shown in the cytocochleogram. (−)-MK-801 decreased outer hair cell loss but threshold shift and inner hair cell loss were not affected. There was significant correlation between threshold shift at 4 kHz and the 8-isoprostane level in the organ of Corti. In the modiolar core, there was a tendency toward correlation, but not for the lateral wall. (+)-MK-801 and PD 174494 decreased threshold shift but did not influence 8-isoprostane levels in the lateral wall; conversely, L-NAME decreased 8-isoprostane level but not threshold shift. Significant correlation was seen between outer and inner hair cell loss and 8-isoprostane in the organ of Corti.

L-NAME decreased 8-isoprostane level in the organ of Corti but had no effect hair cell loss. (+)-MK-801, NAC, and PD 174474 showed some protective effect on inner hair cells. Elevation of 8-isoprostane in the organ of Corti was less with PD 174494 than with the other treatments. In the lateral wall and modiolar core, no significant correlation was seen between hair cell loss and 8-isoprostane.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the relevant fields are intended to be within the scope of the following claims.

We claim:

1. A method of maintaining viability of spiral ganglion cells, comprising:
   i) locally administering in vivo to an ear of an animal with hearing loss, said ear having spiral ganglion cells at risk of degenerating and losing viability a) at least one neurotrophin; and b) a device configured for the administration of continuous electrical stimulation to an ear of an animal;
   ii) administering said continuous electrical stimulation without lapsing below said threshold stimulation in the presence of said neurotrophin under conditions such that said spiral ganglion cells maintain viability.

2. The method of claim 1, wherein said ear is lacking inner hair cells.

3. The method of claim 1, wherein said neurotrophin is selected from the group consisting of glial cell line-derived neurotrophic factor, brain-derived neurotrophic factor, neurotrophin-3, neurotrophin-4/5, and ciliary neurotrophic factor.

4. The method of claim 1, wherein said administered locally is via an osmotic pump implanted in said ear of said animal.

5. The method of claim 1, wherein the viability of said spiral ganglion cells is maintained to a greater extent than the viability seen upon separate administration of said at least one neurotrophin or said continuous electrical stimulation.

6. The method of claim 1, further comprising administering at least one antioxidant.

* * * * *